United States Patent [19]

Vermeer et al.

[11] Patent Number: 5,750,733
[45] Date of Patent: May 12, 1998

[54] HYDROXY CONTAINING ALKYL GLYCAMIDES, LOW FOAMING DETERGENT COMPOSITIONS COMPRISING SUCH AND A PROCESS FOR THEIR MANUFACTURE

[75] Inventors: Robert Vermeer, Nutley; Bijan Harichian, South Orange, both of N.J.

[73] Assignee: Lever Brothers Company, Division of Conopco, Inc., New York, N.Y.

[21] Appl. No.: 689,178

[22] Filed: Aug. 6, 1996

[51] Int. Cl.$^6$ .................. C07D 321/00; C07C 233/00; C11D 3/38; D06M 9/00
[52] U.S. Cl. .................. 549/346; 549/417; 549/476; 564/189; 564/191; 564/193; 564/197; 510/372; 510/383; 510/445; 510/470; 510/502; 510/535
[58] Field of Search ................... 564/189, 191, 564/193, 197; 549/346, 417, 476; 510/372, 383, 445, 470, 502, 535

[56] References Cited

U.S. PATENT DOCUMENTS 3,676,340  7/1972  Berg et al. .................. 252/8.75
5,288,431  2/1994  Huber et al. .................. 252/548
5,318,728  6/1994  Surutzids et al. .................. 252/548

FOREIGN PATENT DOCUMENTS

| 92/06150 | 4/1992 | WIPO . |
| 92/06162 | 4/1992 | WIPO . |
| 93/25647 | 12/1993 | WIPO . |
| 94/12598 | 6/1994 | WIPO . |
| 95/07256 | 3/1995 | WIPO . |
| 95/07341 | 3/1995 | WIPO . |
| 95/20028 | 7/1995 | WIPO . |

*Primary Examiner*—Mukund J. Shah
*Assistant Examiner*—Tamthom T. Ngo
*Attorney, Agent, or Firm*—Ronald A. Koatz

[57] ABSTRACT

The present invention relates to novel hydroxy-containing alkyl glycamide surfactants and detergent composition comprising said surfactants. Since they surprisingly provide low foam, these surfactants can be used as cleansing surfactants in applications where low foaming is desirable.

9 Claims, No Drawings

HYDROXY CONTAINING ALKYL GLYCAMIDES, LOW FOAMING DETERGENT COMPOSITIONS COMPRISING SUCH AND A PROCESS FOR THEIR MANUFACTURE

TECHNICAL FIELD

The present invention is related to a certain novel class of carbohydrate based nonionic surfactant, specifically, hydroxy containing alkyl glycamides and detergent compositions comprising them as well as a process for their manufacture.

BACKGROUND OF THE INVENTION

Most surfactants presently used in detergent and personal product compositions are based on, or derived largely from, petrochemicals. Because of increased concern over environmental issues raised by the use, handling and storage of such materials as well as the continually rising costs of such materials, it would be advantageous to develop surfactants which are instead derived from agriculturally grown substances such as carbohydrates. These naturally occurring compounds represent a source of renewable raw materials which are synthetically versatile, inexpensive, aquatically favorable, optically pure and environmentally friendly. In addition, it is most desirable to have surfactants that provide low foam while simultaneously providing an enhanced solubility in water and in aqueous detergent compositions. This has become a difficult challenge to meet and it is not surprising to find that considerable resource and effort have been directed towards the discovery and development of new surfactants that provide low foam and high solubility characteristics. The patent literature, cosmetic journals and formularies describe many such compounds, however, they still do not provide all the answers to the problems encountered in making a totally satisfactory surfactant, particularly alkyl glycamide surfactants. For one thing, it is known that certain prior art alkyl glycamides exhibit poor water solubility. While not wishing to be bound by theory, it is believed that the amphophilic nature of these compounds cause them to pack closely in the solid state through strong amide/hydroxyl hydrogen bonding as well as strong hydrocarbon Van der Waal forces. The net result is an unfavorable heat of hydration, a high Krafft point, low water solubility (precipitation), a poor rate of micellization and an unfavorable surface tension.

It has now been found that the inclusion of a hydroxyl group on the alkyl chain of a glycamide compound produces a nonionic surfactant that surprisingly exhibits improved water solubility and a low foaming performance. While not wishing to be bound by theory, it is believed that hydroxy containing alkyl glycamide surfactants pack more loosely (favorably) in the solid state through weaker amide/hydroxyl hydrogen bonding and weaker hydrocarbon Van der Waal forces. The net result is a more favorable heat of hydration, a lower Krafft point, an increased water solubility, an enhanced rate of micellization, a low surface tension and low foaming profile.

In addition, it has also been found that the hydroxy containing alkyl glycamide compounds of the present invention represent a novel, naturally derived, biodegradable, class of nonionic surfactant which has surfactant properties equal to, or better than, other well known petrochemically derived surfactants, thereby indicating that they are viable, environmentally sound alternatives to traditional petrochemical surfactants.

These findings are quite unexpected and have not been recognized or appreciated in the art.

BACKGROUND ART

U.S. Pat. No. 5,318,728 describes a method for cleaning fabrics in an automatic washing machine without excessive sudsing comprising from about 100 ppm to about 2% by weight of an N-hexyl polyhydroxy fatty amide surfactant of the formula:

wherein $R^1$ is hexyl, $R^2$ is $C_9$–$C_{17}$ alkyl and Z is $CH_2(CH_2OH)_4CH_2OH$ and from about 3% to about 60% by weight of an auxiliary anionic surfactant selected from the group consisting of $C_{11}$–$C_{16}$ alkyl benzene sulfonates, $C_{12}$–$C_{18}$ primary and secondary alkyl and alkenyl sulfates, and $C_{10}$–$C_8$ alkyl alkoxy sulfates.

This patent teaches N-hexyl alkyl glycamides as low foaming surfactants. There is no teaching or suggestion of the hydroxy containing alkyl glycamides of the present invention as low foaming surfactants.

Furthermore, there is no teaching on suggestion of certain novel hydroxy containing alkyl glycamide surfactants which have low foam, enhance water solubility, lower surface tension and favorable critical micelle concentration relative to other certain prior art alkyl glycamides.

A hydroxy containing alkyl glycamide is defined as an hydroxy alkyl amide of an 1-amino-1-deoxyalditol, 1-amino-1,6-dideoxyalditol or 2-amino-2-deoxyketitol, which in turn, is defined as a sugar substance in which the pseudoaldehyde or pseudoketose group, generally found at the $C_1$ or $C_2$ position of the sugar, has been reduced to an amino group through a reductive amination reaction with ammonia and hydrogen in the presence of a metal catalyst such as nickel. The reaction is typically done in water or organic solvent, but is usually done in a mixture of both. Methods of preparing such glycamines are well known in the art and are described in the J. Chem. Soc. 1682, (1922) to Ling et al.; J. Amer. Chem. Soc. 62, 3315, (1940) to Wayne et al., 72, 5416, (1950) to Holly et al., 79, 3541, (1957) to Kagan et al.; Methods in Carbohydr. Chem. 2, 79, (1963) to Long et al.; U.S. Pat. No. 2,016,962 to Flint et al., U.S. Pat. No. 2,621,175 to Holley et al.; and EP Application No. 0,536,939 to Beck, all of which are incorporated herein by reference.

A hydroxy containing alkyl glycamide can also be defined as an hydroxy dialkyl amide of an 1-alkylamino-1-deoxyalditol, 1-alkylamino-1,6-dideoxyalditol or 2-alkylamino-2-deoxyketitol, which in turn, is defined as a sugar substance in which the pseudoaldehyde or pseudoketose group, generally found at the $C_1$ or $C_2$ position of the sugar, has been reduced to an alkylamino group through a reductive amination reaction with an $C_1$–$C_{28}$ alkylamine and hydrogen in the presence of a metal catalyst such as nickel. The reaction is typically done in water or organic solvent, but is preferably done in a mixture of both. Methods of preparing such glycamines are well known in the art and are described in U.S. Pat. No. 5,334,764 to Scheibel et al., U.S. Pat. No. 2,016,962 to Flint et al., J. Amer. Chem. Soc. 66, 483 (1944) and J. Dispersion Science and Technology 12 (3&4), 227, (1991) all of which are incorporated herein by reference.

Hydroxy containing alkyl glycamide surfactants may be based as compounds comprising one saccharide unit (e.g., galactamides, ribamides, glucamides or fructamides) two saccharide units (e.g., lactamides or maltamides) or more than two saccharide units (e.g., maltotriamides or maltohexamides). Any carbohydrate can be used as long as the sugar has a pseudoaldehyde or pseudoketose group available for reduction to an amine.

While certain alkyl glycamides are known in the art, there is no teaching or suggestion of the hydroxy containing alkyl glycamides of the present invention for use in low sudsing detergent compositions.

More specifically, there is no teaching or suggestion of a certain novel hydroxyl containing alkyl glycamide compounds which have low foam, enhanced water solubility, lower surface tension and favorable critical micelle concentration relative to prior art alkyl glycamides.

In addition, there is no teaching or suggestion of a new method of manufacture of such hydroxyl containing alkyl glycamide compounds.

LOW SUDSING DETERGENT COMPOSITIONS

The formulation of detergent compositions containing typical detersive surfactants necessarily results in products which have, to a more or less degree, the inherent tendency to form suds when the compositions are agitated in an aqueous medium. In many circumstances, the formation of suds is desirable, and consumers have come to expect high, rich suds in various shampoo, personal cleansing and hand dishwashing compositions. On the other hand, in certain other compositions the presence of suds can be problematic. For example, most hard surface cleansers are designed to have low suds levels, thereby obviating the need for extensive rinsing of the surfaces after the cleanser has been applied. Likewise, some washing machines, especially European-style front-loading machines which are designed to use substantially less water than the more familiar American style top-loading machines, typically employ higher concentrations of detersive surfactants. Suds levels must be kept low otherwise the suds can actually spill from such machines. A similar situation occurs with most automatic dishwashing machines where surfactant levels are kept very low and suds controlling agents are used extensively to provide a nearly sudsless cleaning of dishware. Low sudsing can also be advantageous in concentrated laundering processes such as those described in U.S. Pat. Nos. 4,489,455 and 4,489,574, which are incorporated herein by reference.

Considerable attention has lately been directed to the alkyl glycamide nonionic surfactants which exhibit particularly good cleaning performance, especially when used in conjunction with various anionic surfactants. There is considerable impetus to begin using alkyl glycamide surfactants in commercial cleaning compositions of all types.

Unfortunately, many of the alkyl glycamide surfactants are suds boosters and stabilizers, especially when used in combination with conventional anionic surfactants. Accordingly, the formulator of low sudsing detergent compositions either must curtail the use of this desirable class of surfactants when formulating low sudsing detergents, or must use relatively high amounts of suds controlling agents in such compositions.

By the present invention, it has been unexpectedly determined that certain members of the class of alkyl glycamine surfactants, particularly those with a hydroxyl group in the alkyl chain, provide good cleaning performance, but do not undesirably enhance sudsing. Indeed, it has been further discovered that the aforesaid "low sudsing" hydroxy containing alkyl glycamide surfactants can actually diminish the sudsing of their counterpart high sudsing alkyl glycamide surfactants. This sub-class of low sudsing hydroxy containing alkyl glycamide is employed in the practice of this invention to provide low sudsing compositions for use under circumstances where, as disclosed above, low sudsing is desired.

Thus, the ability to find a naturally derived, environmentally friendly, biodegradable, solid sugar based nonionic surfactant that provides low foam, enhanced water solubility, low surface tension, and favorable critical micelle concentration as well as a viable, cost effective, commercially feasible method for their manufacture is a significant achievement.

Accordingly, it is an objective of the present invention to provide novel hydroxy containing alkyl glycamide compounds as surface-active agents.

It is another object of the present invention to provide naturally derived, nonionic hydroxy containing alkyl glycamide surfactants.

It is another object of the present invention to provide nonionic hydroxy containing alkyl glycamide surfactants that dissolve readily in water and have a controllable low foam profile.

It is still another object of the present invention to provide a class of glycamide surfactant which does not become turbid or produce sedimentation upon standing in water or in aqueous low sudsing laundry detergent, automatic dishwashing detergent, and hard surface cleansing compositions.

It is still another object of the present invention to provide nonionic hydroxy containing alkyl glycamide surfactants that have low surface tension and a favorable critical micelle concentration.

It is still another object of the present invention to provide new and improved powdered and liquid detergent compositions which are effective in removing oily soil, grease and stain from fabrics, textile fibers, hard surfaces, eating utensils, kitchenware and the like.

It is still another object of the present invention to provide improved method for cleansing fabrics, textile fibers, hard surfaces, eating utensils, kitchenware and the like.

It is still another object of the present invention to provide a viable, potentially commercially feasible process for the manufacture of nonionic hydroxy containing alkyl glycamide surfactants.

It is a final object of the present invention to prepare solid nonionic hydroxy containing glycamide surfactants in good yield, high purity, and desirable color without hydroxyl group protection, oligomerization or polymerization. These and other objects will become readily apparent from the detailed description which follows.

SUMMARY OF THE INVENTION

One embodiment of the invention relates to a certain novel class of carbohydrate based nonionic surfactant, specifically hydroxy containing alkyl glycamide compounds. These compounds surprisingly exhibit improved water solubility, a controllable low foaming profile, low surface tension and favorable critical micelle concentration.

The second embodiment of the invention relates to novel low sudsing detergent and hard surface cleansing compositions comprising hydroxy containing alkyl glycamide surfactants.

Preferred compositions herein are those which contain an auxiliary detersive surfactant and other detersive adjuncts, as disclosed hereinafter.

The invention also encompasses method for cleaning fabrics in an automatic washing machine without excess sudsing comprising contacting the fabrics to be laundered with an aqueous solution (typically, at least about 100 ppm) of the low sudsing detergent compositions provided herein.

The invention further encompasses a method for cleaning hard surfaces without excessive sudsing, comprising contacting the surface to be cleaned with a low sudsing detergent according to this invention, preferably in the presence of water.

The third embodiment of the invention is directed to preparing solid hydroxy containing alkyl glycamide surfactants in good yield, high purity, and desirable color without hydroxy group protection, oligomerization on polymerization and so the process of manufacture is viable and potentially commercially feasible.

DETAILED DESCRIPTION OF THE INVENTION

The present invention relates to a class of environmentally friendly "green" nonionic carbohydrate based surfactant. In particular one embodiment of the invention describes low sudsing detergent compositions comprising hydroxyl containing alkyl glycamide surfactants.

In another embodiment of the invention, a novel process for the manufacture of hydroxy containing alkyl glycamide surfactants is described. In general the nonionic hydroxy containing alkyl glycamide surfactants are of the formula:

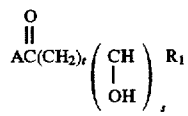

wherein

A represents the following structures which are attached to the carbonyl via the nitrogen (N) atom;

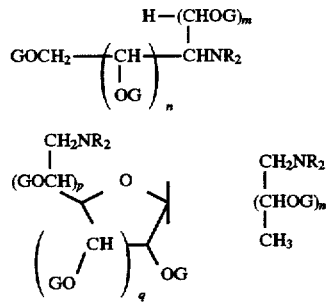

G is hydrogen (H), a $SO_3M$, $PO_3M_2$, $(CH_2CH_2O)_aH$ or $(CH_2CHCH_3O)_bH$ group, a mono-, di-, oligo- or polysaccharide or mixtures thereof;

M is hydrogen (H), an alkali metal, alkaline earth metal, ammonium, alkyl substituted ammonium or mono-, di-, trialkanolammonium group having about 1 to about 5 carbon atoms;
a=0–35
b=0–35
m=0–8
n=1–6
p=0–4
q=0–3
s=1–6
t=0–18

$R_1$ is a straight or branched chain saturated or unsaturated hydrocarbon which may be unsubstituted or substituted with an aromatic, cycloaliphatic or mixed aromatic radical having about 1 to about 31 carbon atoms or hydrogen; and $R_2$ is hydrogen (H), a hydroxylalkyl or alkoxy group having about 1 to about 6 carbon atoms, a straight or branched chain, saturated or unsaturated hydrocarbon which may be unsubstituted or substituted with an aromatic, cycloaliphatic or mixed aromatic aliphatic radical having about 1 to about 28 carbon atoms;

Preferably,

A represents the following structures which are attached to the carbonyl via the nitrogen (N) atoms;

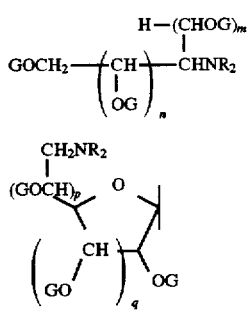

G is hydrogen (H), a $SO_3M$, $PO_3M_2$, $(CH_2CH_2O)_aH$ or $(CH_2CHCH_3O)_bH$ group, a mono-, di- or oligosaccharide or mixtures thereof;

M is hydrogen (H), an alkali metal, alkaline earth metal, ammonium, alkyl substituted ammonium or mono-, di-, trialkanolammonium group having about 1 to about 5 carbon atoms;
a=0–15
b=0–15
m=0–5
n=1–5
p=0–3
q=0–2
s=1–5
t=0–15

$R_1$ is a straight or branched chain saturated or unsaturated hydrocarbon which may be unsubstituted or substituted with an aromatic, cycloaliphatic or mixed aromatic radical having about 1 to about 24 carbon atoms; or hydrogen;

$R_2$ is hydrogen (H), a hydroxylalkyl or alkoxy group having about 1 to about 6 carbon atoms, a straight or branched chain, saturated or unsaturated hydrocarbon which may be unsubstituted or substituted with an aromatic, cycloaliphatic or mixed aromatic aliphatic radical having about 1 to about 18 carbon atoms;

More preferably,

G is hydrogen (H), a $SO_3M$, $PO_3M_2$, $(CH_2CH_2O)_aH$ or $(CH_2CHCH_3O)_bH$ group, a mono- disaccharide or mixtures thereof;

M is hydrogen (H), an alkali metal, alkaline earth metal, ammonium, alkyl substituted ammonium or mono-, di-, trialkanolammonium group having about 1 to 5 carbon atoms;
a=0–5
b=0–5
m=0–3
n=1–4
p=0–2 q=0-2 s=1-4 t=0-10

R₁ is a straight or branched chain saturated or unsaturated hydrocarbon which may be unsubstituted or substituted with an aromatic, cycloaliphatic or mixed aromatic radical having about 1 to about 22 carbon atoms or hydrogen;

R₂ is hydrogen (H), a hydroxyalkyl or alkoxy group having about 1 to about 6 carbon atoms, a straight or branched chain, saturated or unsaturated hydrocarbon which may be unsubstituted or substituted with an aromatic, cycloaliphatic or mixed aromatic aliphatic radical having about 1 to about 16 carbon atoms;

Most preferably,

G is hydrogen (H), group, a mono- or disaccharide or mixtures thereof;

m=0 n=1-3 p=1 q=1 s=1-2 t=0-6

R₁ is a straight or branched chain saturated or unsaturated hydrocarbon which may be unsubstituted or substituted with an aromatic, cycloaliphatic or mixed aromatic radical having about 1 to about 18 carbon atoms or hydrogen;

R₂ is hydrogen (H), a hydroxyalkyl or alkoxy group having about 1 to about 6 carbon atoms, a straight or branched chain, saturated or unsaturated hydrocarbon which may be unsubstituted or substituted with an aromatic, cycloaliphatic or mixed aromatic aliphatic radical having about 1 to about 10 carbon atoms;

A specific example of a monosaccharide hydroxy containing alkyl glycamide compound of the invention is dodecyl 5-hydroxy D-glucamide having the formula:

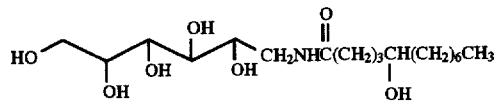

Another specific example of a monosaccharide hydroxy containing alkyl glycamide compound of the invention is octadecyl-9,10-dihydroxy methyl glucamide having the formula:

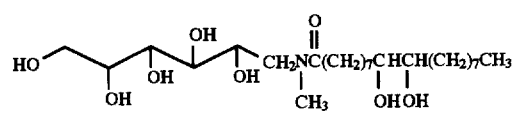

A specific example of a cyclic monosaccharide hydroxy containing alkyl glycamide compound of the invention is undecyl 4-hydroxy D-sorbitan amide having the formula:

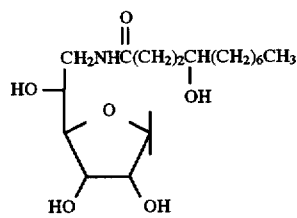

A specific example of a disaccharide alkyl hydroxy containing glycamide compound of the invention is octadecyl-9,10-dihydroxy methyl maltamide having the formula:

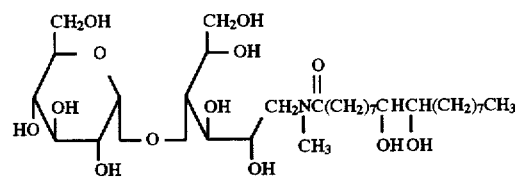

Examples of suitable saccharides that can be reduced to a glycamine include aldotrioses, aldotetroses, aldopentoses, aldohexoses, 6-deoxyaldohexoses, aldoheptoses, ketotrioses, ketopentoses, ketohexoses, ketoheptoses, ketooctoses and ketononoses. Specific example of saccharides that fall within the above classes include, but are not limited to glyceraldehyde, erythrose, threose, ribose, arabinose, xylose, lyxose, allose, altrose, glucose, mannose, gulose, idose, galactose, talose, 6-deoxyallose, 6-deoxyaltrose, 6-deoxyglucose, 6-deoxyglucose, 6-deoxytalose, fucose, rahmnose, glycergalactoheptose, glycerglucoheptose, glycermannoheptose, 1,3-dihydroxy-2-propanone, erythrulose, ribulose, xylulose, psicose, fructose, sorbose, tagatose, alloheptose, altro-3-heptulose, mannoheptulose, sedoheptulose, taloheptulose, glycerogalactooctulose, glycermannooctulose, erythrogalactononulose, erythroglucononulose, sucrose, lactose, maltose, isomaltose, isomalt, isomaltulose (palatinose), α,α-trehalose, cellobiose, gentiobiose, laminarabiose, xylobiose, inulobiose, mannubiose, chondrosine, 3-ketosucrose, leucrose, lactulose, melibiose, turnanose, trehalose, raffinose, planteose, melezitose, gentianose, maltotriose, cellotriose, panose, starchyose, verbascose, cyclohexaamylose, maltoheptanose, cellodextrin, amylose, amylodextrin, dextran, high dextrose corn syrup, high fructose corn syrup, high maltose corn syrup, xylans, mannans, starch, hemicellulose and cellulose. The saccharide may be acyclic or cyclic (including furanose, pyranose, septanose rings or mixtures thereof), have the D or L configuration and contain an α or β glycoside group or mixtures thereof at the anomeric position.

If R₁ or R₂ is interrupted by an aromatic group, the aromatic radical may be for example, benzoyl or aniline. Cycloaliphatic radicals are exemplified, but not limited to cyclopentyl and cyclohexyl. Suitable mixed aromatic aliphatic radicals are exemplified by benzylpropyl, phenylethyl, phenoxyethyl and vinylbenzyl.

The hydroxy containing alkyl glycamide compounds of the present invention can also be ethoxylated, propoxylated or butoxylated with ethylene oxide, propylene oxide, butylene oxide or mixtures thereof to give a series of polyoxyalkylene ether sugar surfactants.

The hydroxy containing alkyl glycamide compounds of the present invention can also be sulfated with chlorosulfonic acid, sulfur trioxide, sulfur trioxide/Lewis base complexes, oleum, sulfuric acid, sulfamic acid and the like as well as mixtures thereof, to give a series of novel sulfated sugar based anionic surfactants.

The hydroxy containing alkyl glycamide compounds of the present invention can also be phosphorylated with phosphorus oxychloride, phosphorous pentoxide, polyphosphoric acid, phosphoric acid, phosphorus trichloride and the like as well as mixtures thereof, to give a series of novel phosphated sugar based esters (mono-, di- and triesters as well as mixtures thereof as anionic surfactants.

If the $R_1$ or $R_2$ group is an aliphatic radical (saturated or unsaturated hydrocarbon), suitable examples include methyl, ethyl, propyl, butyl, pentyl, hexyl, heptyl, octyl, nonyl, decyl, undecyl, dodecyl, isotridecyl, tridecyl, tetradecyl, pentadecyl, hexadecyl, heptadecyl, octadecyl, coco, soya, tallow, tall oil, castor, corn, cottonseed, palm, rapeseed, safflower, sesame, sunflower, fish oil, allyl, octenyl, nonenyl, decenyl, undecenyl, dodecenyl, tridecenyl, tetradecenyl, pentadecenyl, hexadecenyl, heptadecenyl, octadecenyl (oleyl), linoleyl, linolenyl, hydroxymethyl, hydroxyethyl, hydroxypropyl, hydroxybutyl, hydroxypentyl and hydroxyhexyl.

DETERGENT COMPOSITIONS

The essential and less essential components of the present invention are described in detail below.

The Detergent Surfactant

The amount of detergent surfactant included in the detergent compositions of the present invention can vary from about 1% to about 75% by weight of the composition depending upon the particular surfactant(s) used, the type of composition to be formulated (e.g., granular, liquid, etc.) and the effects desired. Preferably, the detergent surfactant(s) comprises from about 5% to about 60% by weight of the composition. The detergent surfactant can be nonionic, anionic, ampholytic, zwitterionic, or cationic. Mixtures of these surfactants can also be used.

A. Nonionic Surfactants

Suitable nonionic surfactants are generally disclosed in U.S. Pat. No. 3,929,678, Laughlin et al., issued Dec. 30, 1975, at column 13, line 14 through column 16, line 6, incorporated herein by reference. Classes of useful nonionic surfactants include:

1. The polyethylene oxide condensates of alkyl phenols. These compounds include the condensation products of alkyl phenols having an alkyl group containing from about 6 to 12 carbon atoms in either a straight chain or branched chain configuration with ethylene oxide, the ethylene oxide being present in an amount equal to from about 5 to about 25 moles of ethylene oxide per mole of alkyl phenol. Examples of compounds of this type include nonyl phenol condensed with about 9.5 moles of ethylene oxide per mole of phenol; dodecyl phenol condensed with about 12 moles of ethylene oxide per mole of phenol; dinonyl phenol condensed with about 15 moles of ethylene oxide per mole of phenol; and diisooctyl phenol condensed with about 15 moles of ethylene oxide per mole of phenol. Commercially available nonionic surfactants of this type include Igepal CO-630, marketed by the GAF Corporation; and Triton X-45, X-114, X-100, and X-102, all marketed by the Rohm & Haas Company.

2. The condensation products of aliphatic alcohols with from about 1 to 25 moles of ethylene oxide. The alkyl chain of the aliphatic alcohol can either be straight or branched, primary or secondary, and generally contains from about 8 to about 22 carbon atoms. Particularly preferred are the condensation products of alcohols having an alkyl group containing from about 10 to about 20 carbon atoms with from about 4 to about 10 moles of ethylene oxide per mole of alcohol. Examples of such ethoxylated alcohols include the condensation product of myristyl alcohol with about 10 moles of ethylene oxide per mole of alcohol; and the condensation product of coconut alcohol (a mixture of fatty alcohols with alkyl chains varying in length from 10 to 14 carbon atoms) with about 9 moles of ethylene oxide. Examples of commercially available nonionic surfactants of this type include Tergitol 15-S-9 (the condensation product of $C_{11-C15}$ linear alcohol with 9 moles ethylene oxide), marketed by Union Carbide Corporation; Neodol 45-9 (the condensation product of $C_{14-C15}$ linear alcohol with 9 moles of ethylene oxide, Neodol 23-6.5 (the condensation product of $C_{12-C13}$ linear alcohol with 6.5 moles of ethylene oxide), Neodol 45-7 (the condensation product of $C_{14-C15}$ linear alcohol with 7 moles of ethylene oxide), and Neodol 45-4 (the condensation product of $C_{14}$–$C_{15}$ linear alcohol with 4 moles of ethylene oxide), marketed by Shell Chemical Company.

3. The condensation products of ethylene oxide with a hydrophobic base formed by the condensation of propylene oxide with propylene glycol. The hydrophobic portion of these compounds has a molecular weight of from about 1500 to about 1800 and exhibits water insolubility. The addition of polyoxyethylene moieties to this hydrophobic portion tends to increase the water solubility of the molecule as a whole, and the liquid character of the product is retained up to the point where the polyoxyethylene content is about 50% of the total weight of the condensation product, which corresponds to condensation with up to about 40 moles of ethylene oxide. Examples of compounds of this type include certain of the commercially available Pluronic surfactants, marketed by Wyandotte Chemical Corporation.

4. The condensation products of ethylene oxide with the product resulting from the reaction of propylene oxide and ethylenediamine. The hydrophobic moiety of these products consists of the reaction product of ethylenediamine and excess propylene oxide, and generally has a molecular weight of from about 2500 to about 3000. This hydrophobic moiety is condensed with ethylene oxide to the extent that the condensation product contains from about 40% to about 80% by weight of polyoxyethylene and has a molecular weight of from about 5,000 to about 11,000. Examples of this type of nonionic surfactant include certain of the commercially available Tetronic compounds, marketed by Wyandotte Chemical Corporation.

5. Semi-polar nonionic surfactants which include water-soluble amine oxides containing one alkyl moiety of from about 10 to about 18 carbon atoms and 2 moieties selected from the group consisting of alkyl groups and hydroxyalkyl groups containing from about 1 to about 3 carbon atoms; water-soluble phosphine oxides containing one alkyl moiety of from about 10 to about 18 carbon atoms and 2 moieties selected from the group consisting of alkyl groups and hydroxyalkyl groups containing from about 1 to about 3 carbon atoms; and water-soluble sulfoxides containing one alkyl moiety of from about 10 to 18 carbon atoms and a moiety selected from the group consisting of alkyl and hydroxyalkyl moieties of from about 1 to 3 carbon atoms.

Preferred semi-polar nonionic detergent surfactants are the amine oxide surfactants having the formula:

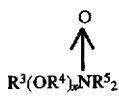

wherein $R^3$ is an alkyl, hydroxyalkyl, or alkyl phenyl group or mixtures thereof containing from about 8 to about 22 carbon atoms; $R^4$ is an alkylene or hydroxyalkylene group containing from about 2 to about 3 carbon atoms or mixtures thereof; x is from 0 to about 3; and each $R^5$ is an alkyl or hydroxyalkyl group containing from about 1 to about 3 carbon atoms or a polyethylene oxide group containing from about 1 to about 3 ethylene oxide groups. $R_5$ groups can be attached to each other, e.g., through an oxygen or nitrogen atom, to form a ring structure.

Preferred amine oxide surfactants are $C_{10}$–$C_{18}$ alkyldimethylamine oxides and $C_8$–$C_{12}$ alkoxyethyldihydroxyethylamine oxides.

6. Alkylpolysaccharides disclosed in U.S. Pat. No. 4,565,647, Llenado, issued Jan. 21, 1986, having a hydrophobic group containing from about 6 to about 30 carbon atoms, preferably from about 10 to about 16 carbon atoms and a polysaccharide, e.g., a polyglycoside, hydrophilic group containing from about 1½ to about 10, preferably from about 1½ to about 3, most preferably from about 1.6 to about 2.7 saccharide units. Any reducing saccharide containing 5 or 6 carbon atoms can be used, e.g., glucose, galactose, and galactosyl moieties can be substituted for the glucosyl moieties. (Optionally the hydrophobic group is attached at the 2-, 3-, 4-, etc. positions thus giving a glucose or galactose as opposed to a glucoside or galactoside). The intersaccharide bonds can be, e.g., between the one position of the additional saccharide units and the 2-, 3-, 4-, and/or 6-positions on the preceding saccharide units.

Optionally, and less desirably, there can be a polyalkylene oxide chain joining the hydrophobic moiety and the polysaccharide moiety. The preferred alkyleneoxide is ethylene oxide. Typical hydrophobic groups include alkyl groups, either saturated or unsaturated, branched or unbranched containing from about 8 to about 18, preferably from about 10 to about 16, carbon atoms. Preferably, the alkyl group is a straight chain saturated alkyl group. The alkyl group can contain up to 3 hydroxy groups and/or the polyalkyleneoxide chain can contain up to about 10, preferably less than 5, alkyleneoxide moieties. Suitable alkyl polysaccharides are octyl, nonyldecyl, undecyldodecyl, tridecyl, tetradecyl, pentadecyl, hexadecyl, heptadecyl, and octadecyl, di-, tri-, tetra-, penta-, and hexaglucosides, galactosides, lactosides, glucoses, fructosides, fructoses and/or galactoses. Suitable mixtures include coconut alkyl, di-, tri-, tetra-, and pentaglucosides and tallow alkyl tetra-, penta-, and hexaglycosides. The preferred alkylpolyglycosides have the formula:

$$R^2O(C_nH_{2n}O)_t(glycosyl)_x$$

wherein $R^2$ is selected from the group consisting of alkyl, alkylphenyl, hydroxyalkyl, hydroxyalkylphenyl, and mixtures thereof in which the alkyl groups contain from about 10 to about 18, preferably from about 12 to about 14, carbon atoms; n is 2 or 3, preferably 2; t is from 0 to about 10, preferably 0; and x is from about 1½ to about 10, preferably from about 1½ to about 3, most preferably from about 1.6 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominately the 2-position.

7. The fatty acid amide surfactants having the formula:

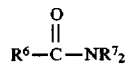

wherein $R^6$ is an alkyl group containing from about 7 to about 21 (preferably from about 9 to about 17) carbon atoms and each $R^7$ is selected from the group consisting of hydrogen, $C_1$–$C_4$ alkyl, $C_1$–$C_4$ hydroxyalkyl, and —$(C_2H_4O)_x$H where x varies from about 1 to about 3.

Preferred amides are $C_8$–$C_{20}$ ammonia amides, monoethanolamides, diethanolamides, and isopropanolamides.

8. The polyhydroxy fatty acid amide surfactants (alkyl glycamides) having the formula:

wherein $R^1$ is H, $C_1$–$C_4$ hydrocarbyl, 2-hydroxyethyl, 2-hydroxypropyl, or a mixture thereof, preferably $C_1$–$C_4$ alkyl, more preferably $C_1$ or $C_2$ alkyl, most preferably $C_1$ alkyl (i.e., methyl); and $R_2$ is a $C_5$–$C_{31}$ hydrocarbyl, preferably straight chain $C_7$–$C_{19}$ alkyl or alkenyl, more preferably straight chain $C_9$–$C_{17}$ alkyl or alkenyl, most preferably straight chain $C_{11}$–$C_{15}$ alkyl or alkenyl, or mixtures thereof; and Z is a polyhydroxyhydrocarbyl having a linear hydrocarbyl chain with at least 3 hydroxyl groups directly connected to the chain, or an alkoxylated derivative (preferably ethoxylated or propoxylated) thereof. Z preferably will be derived from a reducing sugar in a reductive amination reaction; more preferably Z will be a glycityl. Suitable reducing sugars include glucose, fructose, maltose, lactose, galactose, mannose, and xylose. As for raw materials, high dextrose corn syrup, high fructose corn syrup, and high maltose corn syrup can be utilized as well as the individual sugars listed above. These corn syrups may yield a mixture of sugar components for Z. It should be understood that it is by no means intended to exclude other suitable raw materials. Z preferably will be selected from the group consisting of —$CH_2$(CHOH)$_n$CH$_2$OH, —CH(CH$_2$OH)(CHOH)$_{n-1}$CH$_2$OH, —CH$_2$(CHOH)$_2$(CHOR')(CHOH)CH$_2$OH, and alkoxylated derivatives thereof, where n is an integer from 3 to 5, (inclusive) and R' is H or a cyclic or aliphatic monosaccharide. Most preferred are glycityls wherein n is 4, particularly —CH$_2$(CHOH)$_4$CH$_2$OH.

In the above formula $R^1$ can be, for example, N-methyl, N-ethyl, N-propyl, N-isopropyl, N-butyl, N-2-hydroxyethyl, or N-2-hydroxypropyl.

$R^2$—CO—N< can be, for example, cocamide, stearamide, oleamide, lauramide, myristamide, capricamide, palmitamide, tallowamide, etc.

Z can be 1-deoxyglucityl, 2-deoxyfructityl, 1-deoxymaltityl, 1-deoxylactityl, 1-deoxygalactityl, 1-deoxymannityl, 1-deoxymaltotriotityl, etc.

9. The N-alkoxy and N-aryloxy polyhydroxy fatty acid amide surfactants (alkyl glycamides) having the formula:

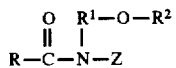

wherein R is $C_7-C_{21}$ hydrocarbyl, preferably $C_9-C_{17}$ hydrocarbyl, including straight-chain (preferred), branched-chain alkyl and alkenyl, as well as substituted alkyl and alkenyl, e.g., 12-hydroxyoleic, or mixtures thereof; $R^1$ is $C_2-C_8$ hydrocarbyl including straight-chain, branched-chain and cyclic (including aryl), and is preferably $C_2-C_4$ alkylene, i.e., $-CH_2CH_2-$, $-CH_2CH_2CH_2-$ and $-CH_2(CH_2)_2CH_2-$; $R^2$ is $C_1-C_8$ straight-chain, branched-chain and cyclic hydrocarbyl including aryl and oxyhydrocarbyl, and is preferably $C_1-C_4$ alkyl or phenyl; and Z is a polyhydroxyhydrocarbyl moiety having a linear hydrocarbyl chain with at least 2 (in the case of glyceraldehyde) or at least 3 hydroxyls (in the case of other reducing sugars) directly connected to the chain, or an alkoxylated derivative (preferably ethoxylated or propoxylated) thereof. Z preferably will be derived from a reducing sugar in a reductive amination reaction; more preferably Z is a glycityl moiety. Suitable reducing sugars include glucose, fructose, maltose, lactose, galactose, mannose, and xylose, as well as glyceraldehyde. As for raw materials, high dextrose corn syrup, high fructose corn syrup, and high maltose corn syrup can be utilized as well as the individual sugars listed above. These corn syrups may yield a mix of sugar components for Z. It should be understood that it is by no means intended to exclude other suitable raw materials. Z preferably will be selected from the group consisting of $-CH_2(CHOH)_nCH_2OH$, $-CH(CH_2OH)(CHOH)_{n-1}-CH_2OH$, $-CH_2-(CHOH)_2(CHOR')(CHOH)CH_2OH$, where n is an integer from 1 to 5, inclusive, and R' is H or a cyclic mono- or polysaccharide, and alkoxylated derivatives thereof. Most preferred are glycityls wherein n is 4, particularly $-CH_2-(CHOH)_4-CH_2OH$.

In compounds of the above formula, nonlimiting examples of the amine substituents group $-R^1O-R^2$ can be, for example: 2-methoxyethyl-, 3-methoxypropyl-, 4-methoxybutyl-, 5-methoxypentyl-, 6-methoxyhexyl-, 2-ethoxyethyl-, 3-ethoxypropyl-, 2-methoxypropyl, methoxybenzyl-, 2-isopropoxyethyl-, 3-isopropoxypropyl-, 2-(t-butoxy)ethyl-, 3-(t-butoxy)propyl-, 2-(isobutoxy)ethyl-, 3-(isobutoxy)propyl-, 3-butoxypropyl, 2-butoxyethyl, 2-phenoxyethyl-, methoxycyclohexyl-, methoxycyclohexylmethyl-, tetrahydrofurfuryl-, tetrahydropyranyloxyethyl-, 3-[2-methoxyethoxy]propyl-, 2-[2-methoxyethoxy]ethyl-, 3-[3-methoxypropoxy]propyl-, 2-[3-methoxypropoxy]ethyl-, 3-[methoxypolyethyleneoxy]propyl-, 3-[4-methoxybutoxy]propyl-, 3-[2-methoxyisopropoxy]propyl-, $CH_3OCH_2CH(CH_3)-$ and $CH_3OCH_2CH(CH_3)CH_2O(CH_2)_3-$.

R—CO—N< can be, for example, cocamide, stearamide, oleamide, lauramide, myristamide, capricamide, palmitamide, tallowamide, ricinolamide, etc.

Z can be 1-deoxyglucityl, 2-deoxyfructityl, 1-deoxymaltityl, 1-deoxylactityl, 1-deoxygalactityl, 1-deoxymannityl, 1-deoxymaltotriotityl, etc.

10. The aldonamides and aldobionamides disclosed in U.S. Pat. Nos. 5,296,588; 5,336,765; 5,386,018; 5,389,279; 5,401,426 and 5,401,839 as well as WO 94/12511 which are all incorporated herein by reference.

Aldobionamides are defined as the amide of an aldobionic acid (or aldobionolactone) and an aldobionic acid is a sugar substance (e.g., any cyclic sugar comprising at least two saccharide units) wherein the aldehyde group (generally found at the $C_1$ position of the sugar) has been replaced by a carboxylic acid, which upon drying cyclizes do an aldonolactone.

An aldobionamide may be based on compounds comprising two saccharide units (e.g., lactobionamides or maltobionamides, etc.) or they may be based on compounds comprising more than two saccharide units (e.g., maltotrionamides), as long as the terminal sugar in the polysaccharide has an aldehyde group. By definition an aldobionamide must have at least two saccharide units and cannot be linear. Disaccharide compounds such as lactobionamides or maltobionamides are preferred compounds. Other examples of aldobionamides (disaccharides) which may be used include cellobionamides, melibionamides and gentiobionamides.

A specific examples of an aldobionamide which may be used for purposes of the invention is the disaccharide lactobionamide set forth below:

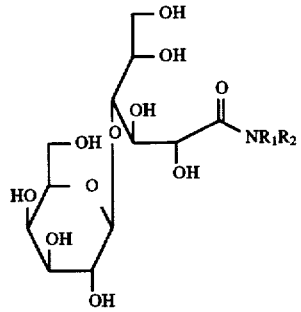

wherein $R_1$ and $R_2$ are the same or different and are selected from the group consisting of hydrogen; an aliphatic hydrocarbon radical (e.g., alkyl groups and alkene groups which groups may contain heteroatoms such as N, O or S or alkoxylated alkyl chains such as ethoxylated or propoxylated alkyl groups, preferably an alkyl group having 6 to 24, preferably 8 to 18 carbons; an aromatic radical (including substituted or unsubstituted aryl groups and arenes); a cycloaliphatic radical; an amino acid ester, ether amines and mixtures thereof. It should be noted that $R_1$ and $R_2$ cannot be hydrogen at the same time.

B. Anionic Surfactants

Anionic surfactants suitable for use in the present invention are generally disclosed in U.S. Pat. No. 3,929,678, Laughlin et al., issued Dec. 30, 1975, at column 23, line 58 through column 29, line 23, incorporated herein by reference. Classes of useful anionic surfactants include:

1. Ordinary alkali metal soaps, such as the sodium, potassium, ammonium and alkylolammonium salts of higher fatty acids containing from about 8 to about 24 carbon atoms, preferably from about 10 to about 20 carbon atoms. Preferred alkali metal soaps are sodium laurate, sodium cocoate, sodium stearate, sodium oleate and potassium palmitate as well as fatty alcohol ether methylcarboxylates and their salts.

2. Water-soluble salts, preferably the alkali metal, ammonium and alkylolammonium salts, of organic sulfuric reaction products having in their molecular structure an alkyl group containing from about 10 to about 20 carbon atoms and a sulfonic acid or sulfuric acid ester group. (Included in the term "alkyl" is the alkyl portion of acyl groups).

Examples of this group of anionic surfactants are the sodium and potassium alkyl sulfates, especially those obtained by sulfating the higher alcohol ($C_8$–$C_{18}$ carbon atoms) such as those produced by reducing the glycerides of tallow or coconut oil; and the sodium and potassium alkylbenzene sulfonates in which the alkyl group contains from about 9 to about 15 carbon atoms, in straight chain or branched chain configuration, e.g., those of the type described in U.S. Pat. No. 2,220,099, Guenther et al., issued Nov. 5, 1940, and U.S. Pat. No. 2,477,383, Lewis, issued Dec. 26, 1946. Especially useful are linear straight chain alkylbenzene sulfonates in which the average number of carbon atoms in the alkyl group is from about 11 to about 13, abbreviated as $C_{11}$–$C_{13}$ LAS.

Another group of preferred anionic surfactants of this type are the alkyl polyalkoxylate sulfates, particularly those in which the alkyl group contains from about 8 to about 22, preferably from about 12 to about 18 carbon atoms, and wherein the polyalkoxylate chain contains from about 1 to about 15 ethoxylate and/or propoxylate moieties, preferably from about 1 to about 3 ethoxylate moieties. These anionic detergent surfactants are particularly desirable for formulating heavy-duty liquid laundry detergent compositions.

Other anionic surfactants of this type include sodium alkyl glyceryl ether sulfonates, especially those ethers of higher alcohols derived from tallow and coconut oil; sodium coconut oil fatty acid monoglyceride sulfonates and sulfates; sodium or potassium salts of alkyl phenol ethylene oxide ether sulfates containing from about 1 to about 10 units of ethylene oxide per molecule and wherein the alkyl groups contain from about 8 to about 12 carbon atoms; and sodium or potassium salts of alkyl ethylene oxide ether sulfates containing about 1 to about 15 units of ethylene oxide per molecule and wherein the alkyl group contains from about 8 to about 22 carbon atoms.

Also included are water-soluble salts of esters of alpha sulfonated fatty acids containing from about 6 to about 20 carbon atoms in the fatty acid group and from about 1 to about 10 carbon atoms in the ester group; water-soluble salts of 2-acyloxyalkane-1-sulfonic acids containing from about 2 to about 9 carbon atoms in the acyl group and from about 9 to about 23 carbon atoms in the alkane moiety; water-soluble salts of olefin sulfonates containing from about 12 to about 24 carbon atoms; and beta alkyloxy alkane sulfonates containing from about 1 to about 3 carbon atoms in the alkyl group and from about 8 to about 20 carbon atoms in the alkane moiety as well as primary alkane sulfonates, secondary alkane sulfonates, α-sulfo fatty acid esters, sulfosuccinic acid alkyl esters, acylaminoalkane sulfonates (Taurides), sarcosinates and sulfated alkyl glycamides, sulfated alkyl aldonamides, and sulfated alkyl polyglycosides.

Particularly preferred surfactants for use herein include alkyl benzene sulfonates, alkyl sulfates, alkyl polyethoxy sulfates and mixtures thereof. Mixtures of these anionic surfactants with a nonionic surfactant selected from the group consisting of $C_{10}$–$C_{20}$ alcohols ethoxylated with an average of from about 4 to about 10 moles of ethylene oxide per mole of alcohol are particularly preferred.

3. Anionic phosphate surfactants such as the alkyl phosphates and alkyl ether phosphates.

4. N-alkyl substituted succinamates.

C. Ampholytic Surfactants

Ampholytic surfactants can be broadly described as aliphatic derivatives of secondary or tertiary amines, or aliphatic derivatives of heterocyclic secondary and tertiary amines in which the aliphatic radical can be straight or branched chain and wherein one of the aliphatic substituents contains from about 8 to about 18 carbon atoms and at least one of the aliphatic substituents contains an anionic water-solubilizing group, e.g., carboxy, sulfonate or sulfate. See U.S. Pat. No. 3,929,678, Laughlin et al., issued Dec. 30, 1975, column 19, line 38 through column 22, line 48, incorporated herein by reference, for examples of ampholytic surfactants useful herein.

D. Zwitterionic Surfactants

Zwitterionic surfactants can be broadly described as derivatives of secondary and tertiary amines, derivatives of heterocyclic secondary and tertiary amines, or derivatives of quaternary ammonium, quaternary phosphonium or tertiary sultonium compounds. See U.S. Pat. No. 3,929,678, Laughlin et al., issued Dec. 30, 1975, column 19, line 38 through column 22, line 48, incorporated herein by reference, for examples of zwitterionic surfactants useful herein.

E. Cationic Surfactants

Cationic surfactants can also be included in detergent compositions of the present invention. Cationic surfactants comprise a wide variety of compounds characterized by one or more organic hydrophobic groups in the cation and generally by a quaternary nitrogen associated with an acid radical. Pentavalent nitrogen ring compounds are also considered quaternary nitrogen compounds. Suitable anions are halides, methyl sulfate and hydroxide. Tertiary amines can have characteristics similar to cationic surfactants at washing solutions pH values less than about 8.5.

Suitable cationic surfactants include the quaternary ammonium surfactants having the formula:

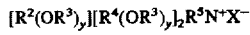

$$[R^2(OR^3)_y][R^4(OR^3)_y]_2R^5N^+X^-$$

wherein $R_2$ is an alkyl or alkyl benzyl group having from about 8 to about 18 carbon atoms in the alkyl chain; each $R_3$ is independently selected from the group consisting of —$CH_2CH_2$—, —$CH_2CH(CH_3)$—, —$CH_2CH(CH_2OH)$—, and —$CH_2CH_2CH_2$—, each $R^4$ is independently selected from the group consisting of $C_1$–$C_4$ alkyl, $C_1$–$C_4$ hydroxyalkyl, benzyl, ring structures formed by joining the two $R^4$ groups, —$CH_2CHOHCHOHCOR^6CHOHCH_2OH$ wherein $R^6$ is any hexose or hexose polymer having a molecular weight less than about 1000, and hydrogen when y is not 0; $R_5$ is the same as $R^4$ or is an alkyl chain wherein the total number of carbon atoms of $R^2$ plus $R^5$ is not more than about 18, each y is from 0 to about 10 and the sum of the y values is from 0 to about 15; and X is any compatible anion.

Preferred examples of the above compounds are the alkyl quaternary ammonium surfactants, especially the monolong chain alkyl surfactants described in the above formula when $R^5$ is selected from the same groups as $R^4$. The most preferred quaternary ammonium surfactants are the chloride, bromide, and methylsulfate $C_8$–$C_{16}$ alkyl trimethylammonium salts, $C_8$–$C_{16}$ alkyl di(hydroxyethyl)methylammonium salts, the $C_8$–$C_{16}$ alkyloxypropyltrimethylammonium salts. Of the above, decyl trimethylammonium methylsulfate, lauryl trimethylammonium chloride, myristyl trimethylammonium bromide and coconut trimethylammonium chloride and methylsulfate are particularly preferred.

A more complete disclosure of cationic surfactants useful herein can be found in U.S. Pat. No. 4,228,044, Cambre, issued Oct. 14, 1980, incorporated herein by reference.

Detergent Builders

Detergent compositions of the present invention contain inorganic and/or organic detergent builders to assist in mineral hardness control. These builders comprise from about 5% to about 80% by weight of the compositions. Built liquid formulations preferably comprise from about 7% to about 30% by weight of detergent builder, while built granular formulations preferably comprise from about 10% to about 50% by weight of detergent builder.

Suitable detergent builders include crystalline aluminosilicate ion exchange materials having the formula:

$$Na_y[(AlO_2)_z(SiO_2)_y]\cdot xH_2O$$

wherein z and y are at least about 6, the mole ratio of z to y is from about 1.0 to about 0.5; and x is from about 10 to about 264. Amorphous hydrated aluminosilicate materials useful herein have the empirical formula $$M_z(zAlO_2 ySiO_2)$$

wherein M is sodium, potassium, ammonium, or substituted ammonium, z is from about 0.5 to about 2; and y is 1; this material having a magnesium ion exchange capacity of at least about 50 milligram equivalents of $CaCO_3$ hardness per gram of anhydrous aluminosilicate.

The aluminosilicate ion exchange builder materials are in hydrated form and contain from about 10% to about 2% of water by weight if crystalline, and potentially even higher amounts of water if amorphous. Highly preferred crystalline aluminosilicate ion exchange materials contain from about 18% to about 22% water in their crystal matrix. The preferred crystalline aluminosilicate ion exchange materials are further characterized by a particle size diameter of from about 0.1 micron to about 10 microns. Amorphous materials are often smaller, e.g., down to less than about 0.01 micron. More preferred ion exchange materials have a particle size diameter of from about 0.2 micron to about 4 microns. The term "particle size diameter" represents the average particle size diameter of a given ion exchange material as determined by convdeterminationytical techniques such as, for example, microscopic determination utilizing a scanning electron microscope. The crystalline aluminosilicate ion exchange materials are usually further characterized by their calcium ion exchange capacity, which is at least about 200 mg. equivalent of $CaCO_3$ water hardness/g of aluminosilicate, calculated on an anhydrous basis, and which generally is in the range of from about 300 mg eq/g to about 352 mg eq/g. The aluminosilicate ion exchange materials are still further characterized by their calcium ion exchange rate which is at least about 2 grains $Ca^{++}$/gallon/minute/gram/gallon of aluminosilicate (anhydrous basis), and generally lies within the range of from about 2 grains/gallon/minute/gram/gallon to about 6/grains/gallon/minute/gram/gallon, based on calcium ion hardness. Optimum aluminosilicates for builder purposes exhibit a calcium ion exchange rate of at least about 4 grains/gallon/minute/gram/gallon.

The amorphous aluminosilicate ion exchange materials usually have a $Mg^{++}$ exchange capacity of at least about 50 mg eq $CaCo_3$/g (12mg $Mg^{++}$/g) and a $Mg^{++}$ exchange rate of at least about 1 grain/gallon/minute/gram/gallon. Amorphous materials do not exhibit an observable diffraction pattern when examined by Cu radiation (1.54 Angstrom Units).

Useful aluminosilicate ion exchange materials are commercially available. These aluminosilicates can be crystalline or amorphous in structure and can be naturally-occurring aluminosilicates or synthetically derived. A method for producing aluminosilicate ion exchange materials is disclosed in U.S. Pat. No. 3,985,669, Krummel et al., issued Oct. 12, 1976, incorporated herein by reference. Preferred synthetic crystalline aluminosilicate ion exchange materials useful herein are available under the designations Zeolite A, Zeolite P (B), and Zeolite X. In an especially preferred embodiment, the crystalline aluminosilicate ion exchange material has the formula:

$$Na_{12}[(AlO_2)_{12}(SiO_2)_{12}]\cdot xH_2O$$

wherein x is from about 20 to about 30, especially about 27.

Other detergency builders useful in the present invention include the alkali metal silicates, alkali metal carbonates, phosphates, polyphosphates, phosphonates, polyphosphonic acids, $C_{10-18}$ alkyl monocarboxylic acids, polycarboxylic acids, alkali metal ammonium or substituted ammonium salts thereof and mixtures thereof. Preferred are the alkali metal, especially sodium, salts of the above.

Specific examples of inorganic phosphate builders are sodium and potassium tripolyphosphate, pyrophosphate, polymeric metaphate having a degree of polymerization of from about 6 to about 21, and orthophosphate. Examples of polyphosphonate builders are the sodium and potassium salts of ethylene-1,1-diphosphonic acid, the sodium and potassium salts of ethane 1-hydroxy-1,1-diphosphonic acid and the sodium and potassium salts of ethane 1,1,2-triphosphonic acid. Other suitable phosphorus builder compounds are disclosed in U.S. Pat. No. 3,159,571, Diehl, issued Dec. 1, 1964; U.S. Pat. No. 3,213,030, Diehl, issued Oct. 19, 1965; U.S. Pat. No. 3,400,148, Quimby, issued Sep. 3, 1968; U.S. Pat. No. 3,400,176, Quimby, issued Sep. 3, 1968; U.S. Pat. No. 3,422,021, Roy, issued Jan. 14, 1969; and U.S. Pat. No. 3,422,137, Quimby, issued Sep. 3, 1968; all herein incorporated by reference. However, while suitable for use in compositions of the invention, one of the advantages of the present invention is that effective detergent compositions can be formulated using minimum levels or in the complete absence of phosphonates and phosphates.

The DDSS sequestrants will provide improved stain and soil removal benefits in the presence and absence of phosphonate and/or phosphate builders or chelants.

Examples of nonphosphorus, inorganic builders are sodium and potassium carbonate, bicarbonate, sesquicarbonate, tetraborate decahydrate, and silicate having a mole ratio of $SiO_2$ to alkali metal oxide of from about 0.5 to about 4.0, preferably from about 1.0 to about 2.4.

Useful water-soluble, nonphosphorus organic builders include the various alkali metal, ammonium and substituted ammonium polyacetates, carboxylates, polycarboxylates and polyhydroxysulfonates. Examples of polyacetate and polycarboxylate builders are the sodium, potassium, lithium, ammonium and substituted ammonium salts of ethylenediamine tetraacetic acid, nitrilotriacetic acid, oxydisuccinic acid, mellitic acid, benzene polycarboxylic acids, and citric acid. For purposes of defining the invention, the organic detergent builder component which may be used herein does not comprise diaminoalkyl di(sulfosuccinate) (DDSS) or salts thereof.

Highly preferred polycarboxylate builders are disclosed in U.S. Pat. No. 3,308,067, Diehl, issued Mar. 7, 1967, incorporated herein by reference. Such materials include the water-soluble salts of homo- and copolymers of aliphatic carboxylic acids such as maleic acid, itaconic acid, mesaconic acid, fumaric acid, aconitic acid, citraconic acid and methylenemalonic acid.

Other builders include the carboxylated carbohydrates disclosed in U.S. Pat. No. 3,723,322, Diehl, issued Mar. 28, 1973, incorporated by reference herein.

A class of useful phosphorus-free detergent builder materials have been found to be ether polycarboxylates. A number of ether polycarboxylates have been disclosed for use as detergent builders. Examples of useful ether polycarboxylates include oxydisuccinate, as disclosed in Berg, U.S. Pat. No. 3,128,287, issued Apr. 7, 1964, and Lamberti et al., U.S. Pat. No. 3,635,830, issued Jan. 18, 1972, both of which are incorporated herein by reference.

A specific type of ether polycarboxylates useful as builders in the present invention are those having the general formula:

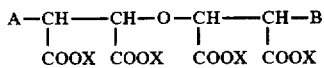

wherein A is H or OH; B is H or

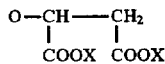

and X is H or a salt-forming cation. For example, if in the above general formula A and B are both H, then the compound is oxydisuccinic acid and its water-soluble salts. If A is OH and B is H, then the compound is tartrate monosuccinic acid (TMS) and its water soluble salts. If A is H and B is

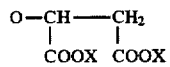

then the compound is tartrate disuccinic acid (TDS) and its water-soluble salts. Mixtures of these builders are especially preferred for use herein. Particularly preferred are mixtures of TMS and TDS in a weight ratio of TMS to TDS of from about 97:3 to about 20:80.

Suitable ether polycarboxylates also include cyclic compounds, particularly alicyclic compounds, such as those described in U.S. Pat. Nos. 3,923,679; 3,835,163; 4,158,635; 4,120,874 and 4,102,903, all of which are incorporated herein by reference.

Other useful detergency builders include the ether hydroxypolycarboxylates represented by the structure:

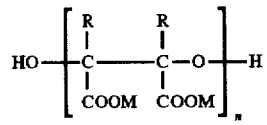

wherein M is hydrogen or a cation wherein the resultant salt is water soluble, preferably an alkali metal, ammonium or substituted ammonium cation, n is from about 2 to about 15 (preferably n is from about 2 to about 10, more preferably n averages from about 2 to about 4) and each R is the same or different and selected from hydrogen, $C_{1-4}$ alkyl or $C_{1-4}$ substituted alkyl (preferably R is hydrogen).

Also suitable in the detergent compositions of the present invention are the 3,3-dicarboxy-4-oxa-1,6-hexanedioates and the related compounds disclosed in U.S. Pat. No. 4,566,984, Bush, issued Jan. 28, 1986, incorporated herein by reference. Other useful builders include the $C_5$–$C_{20}$ alkyl succinic acids and salts thereof. A particularly preferred compound of this type is dodecenylsuccinic acid.

Useful builders also include sodium and potassium carboxymethyloxy-malonate, carboxymethyloxysuccinate, cis-cyclohexanehexacarboxylate, cis-cyclopentanetetracarboxylate, phloroglucinol trisulfonate, water soluble poly-acrylates (having molecular weights of from about 2,000 to about 200,000, for example), and the copolymers of maleic anhydride with vinyl methyl ether or ethylene.

Other suitable polycarboxylates are the polyacetal carboxylates disclosed in U.S. Pat. No. 4,144,226, Crutchfield et al., issued Mar. 13, 1979, incorporated herein by reference. These polyacetal carboxylates can be prepared by bringing together, under polymerization conditions, an ester of glyoxylic acid and a polymerization initiator. The resulting polyacetal carboxylate ester is then attached to chemically stable end groups to stabilize the polyacetal carboxylate against rapid depolymerization in alkaline solution, converted to the corresponding salt, and added to a surfactant.

Especially useful detergency builders include the $C_{10}$–$C_{18}$ alkyl monocarboxylic (fatty) acids and salts thereof. These fatty acids can be derived from animal and vegetable fats and oils, such as tallow, coconut oil and palm oil. Suitable saturated fatty acids can also be synthetically prepared (e.g., via the oxidation of petroleum or by hydrogenation of carbon monoxide via the Fisher-Tropsch process). Particularly preferred $C_{10}$–$C_{18}$ alkyl monocarboxylic acids are saturated coconut fatty acids, palm kernel fatty acids, and mixtures thereof.

Other useful detergency builder materials are the "seeded builder" compositions disclosed in Belgian Patent No. 798,836, published Oct. 29, 1973, incorporated herein by reference. Specific examples of such seeded builder mixtures are 3:1 wt. mixtures of sodium carbonate and calcium carbonate having 5 micron particle diameter; 2.7:1 wt. mixtures of sodium sesquicarbonate and calcium carbonate having a particle diameter of 0.5 microns; 20:1 wt. mixtures of sodium sesquicarbonate and calcium hydroxide having a particle diameter of 0.01 micron; and a 3:3:1 wt. mixture of sodium carbonate, sodium aluminate and calcium oxide having a particle diameter of 5 microns.

Bleaching Compounds—Bleaching Agents and Bleach Activators

The detergent compositions herein may optionally contain bleaching agents or bleaching compositions containing a bleaching agent and one or more bleach activators. When present, bleaching agents will typically be at levels of from about 1% to about 20%, more typically from about 1% to about 10%, of the detergent composition, especially for fabric laundering. If present, the amount of bleach activators will typically be from about 0.1% to about 60%, more typically from about 0.5% to about 40% of the bleaching composition comprising the bleaching agent-plus-bleach activator.

The bleaching agents used herein can be any of the bleaching agents useful for detergent compositions in textile cleaning, hard surface cleaning, or other cleaning purposes that are now known or become known. These include oxygen bleaches as well as other bleaching agents. Perborate bleaches, e.g., sodium perborate (e.g., mono- or tetra-hydrate) can be used herein, but, under some conditions, may undesirably interact with the polyol nonionic surfactant.

One category of bleaching agent that can be used without restriction encompasses percarboxylic ("percarbonate") acid bleaching agents and salts therein. Suitable examples of this class of agents include magnesium monoperoxyphthalate hexahydrate, the magnesium salt of meta-chloro perbenzoic acid, 4-nonylamino-4-oxoperoxybutyric acid and diperoxydodecanedioic acid. Such bleaching agents are disclosed in U.S. Pat. No. 4,483,781, Hartman, issued Nov. 20, 1984, U.S. patent application Ser. No. 740,446, Burns et al., filed Jun. 3, 1985, European Patent Application 0,133,354, Banks et al., published Feb. 20, 1985, and U.S. Pat. No. 4,412,934, Chung et al., issued Nov. 1, 1983. Highly preferred bleaching agents also include 6-nonylamino-6-oxoperoxycaproic acid as described in U.S. Pat. No. 4,634,551, issued Jan. 6, 1987 to Burns et al.

Peroxygen bleaching agents can also be used. Suitable peroxygen bleaching compounds include sodium carbonate peroxyhydrate, sodium pyrophosphate peroxyhydrate, urea peroxyhydrate, and sodium peroxide. Persulfate bleach (e.g., OXONE, manufactured commercially by DuPont) can also be used.

Mixtures of bleaching agents can also be use.

Peroxygen bleaching agents and the perborates are preferably combined with bleach activators, which lead to the in situ production in aqueous solution (i.e., during the washing process) of the peroxy acid corresponding to the bleach activator. Various nonlimiting examples of activators are disclosed in U.S. Pat. No. 4,915,854, issued Apr. 10, 1990 to Mao et al., and U.S. Pat. No. 4,412,934. The nonanoyloxybenzene sulfonate (NOBS) and tetracetyl ethylene diamine (TAED) activators are typical, and mixtures thereof can also be used. See also U.S. Pat. No. 4,634,551 for other typical bleaches and activators useful herein.

Bleaching agents other than oxygen bleaching agents are also known in the art and can be utilized herein. One type of nonoxygen bleaching agent of particular interest includes photoactivated bleaching agents such as the sulfonated zinc and/or aluminum phthalocyanimes. See U.S. Pat. No. 4,033,718, issued Jul. 5, 1977 to Holcombe et al. Typically, detergent compositions will contain about 0.025% to about 1.25%, by weight, of sulfonated zinc phthalocyanine.

Enzymes

Enzymes can be included in the formulations herein for a wide variety of fabric laundering purposes, including removal of protein-based, carbohydrate-based, or triglyceride-based stains, for examples, and for the prevention of refugee dye transfer, and for fabric restoration. The enzymes to be incorporated include proteases, amylases, lipases, cellulases, and peroxidases, as well as mixtures thereof. Other types of enzymes may also be included. They may be of any suitable origin, such as vegetable, animal, bacterial, fungal and yeast origin. However, their choice is governed by several factors such as pH-activity and/or stability optima, thermostability, stability versus active detergents, builders and so on. In this respect bacterial or fungal enzymes are preferred, such as bacterial amylases and proteases, and fungal cellulases.

Enzymes are normally incorporated at levels sufficient to provide up to about 5 mg by weight, more typically about 0.01 mg to about 3 mg, of active enzyme per gram of the composition. Stated otherwise, the compositions herein will typically comprise from about 0.001% to about 5%, preferably 0.01%–1%, by weight of a commercial enzyme preparation. Protease enzymes are usually present in such commercial preparations at levels sufficient to provide from 0.005 to 0.1 Anson units (AU) of activity per gram of composition.

Suitable examples of proteases are the subtilisins which are obtained from particular strains of *B. subtilis* and *B. licheniformis*. Another suitable protease is obtained from a strain of Bacillus, having maximum activity throughout the pH range of 8–12, developed and sold by Novo Industries A/S under the registered trade name ESPERASE. The preparation of this enzyme and analogous enzymes is described in British Patent Specification No. 1,243,784 of Novo. Proteolytic enzymes suitable for removing protein-based stains that are commercially available include those sold under the tradenames ALCALASE and SAVINASE by Novo Industries A/S (Denmark) and MAXATASE by International Bio-Synthetics, Inc. (The Netherlands). Other proteases include Protease A (See European Patent Application No. 130 756 published Jan. 9, 1985) and Protease B (See European Patent Application Serial No. 87303761.8 filed Apr. 28, 1987, and European Patent Application No. 130 756, Bott et al., published Jan. 9, 1985).

Amylases include, for example, a-amylases described in British Patent Specification No. 1,296,839 (Novo), RAPIDASE, Internation Bio-Synthetics, Inc. and TERMAMYL, Novo Industries.

The cellulases usable in the present invention include both bacterial or fungal cellulase. Preferably, they will have a pH optimum of between 5 and 9.5. Suitable cellulases are disclosed in U.S. Pat. No. 4,435,307, Barbesgoard et al., issued Mar. 6, 1984, which discloses fungal cellulase produced from *Humicola insolens* and Humicola strain DSM1800 or a cellulase 212-producing fungus belonging to the genus Aeromonas, and cellulase extracted from the hepatopancreas of a marine mollusk (Dolabella Auricula Solander). Suitable cellulases are also disclosed in GB A-2.075,028; GB A-2,095,275 and DE-OS-2,247,832.

Suitable lipase enzymes for detergent usage include those produced by microorganisms of the Pseudomonas group, such as *Pseudomonas stutzeri* ATCC19,154, as disclosed in British Patent 1,372,034. See also lipases in Japanese Patent Application 53-20487, laid open to public inspection on Feb. 24, 1978. This lipase is available from Amano Pharmaceutical Co. Ltd., Nagoya, Japan, under the tradename Lipase P "Amano", hereinafter referred to as "Amano-P". Other commercial lipases include Amano-CES, lipases ex *Chromobacter viscosum*, e.g., *Chromobacter viscosum* var. lipolyticum NRRLB 3673, commercially available from Toyo Jozo Co., Tagata, Japan; and further *Chromobacter viscosum* lipases from U.S. Biochemical Corp., U.S.A. and Disoynth Co., The Netherlands, and lipases ex *Pseudomonas gladioli*. The LIPOLASE enzyme derived from *Humicola lanuginosa* and commercially available from Novo (See also EPO 341,947) is a preferred lipase for use herein.

Peroxidase enzymes are used in combination with oxygen sources, e.g., percarbonate, perborate, persulfate, hydrogen peroxide, etc. They are used for "solution bleaching", i.e., to prevent transfer of dyes or pigments removed from substrates during wash operations to other substrates in the wash solution. Peroxidase enzymes are known in the art, and include, for examples, horseradish peroxidase, ligninase, and haloperoxidase such as chloro- and bromoperoxidase. Peroxidase-containing detergent compositions are disclosed, for example, in PCT International Application WO 89/099813, published Oct. 19, 1989 by O. Kirk, assigned to Novo Industries A/S.

A wide range of enzyme materials and means for their incorporation into synthetic detergent granules are also disclosed in U.S. Pat. No. 3,553,139, issued Jan. 5, 1971, to McCarty et al. Enzymes are further disclosed in U.S. Pat. No. 4,101,457, Place et al., issued Jul. 18, 1978, and in U.S. Pat. No. 4,507,219, Hughes, issued Mar. 26, 1985, both. Enzyme materials useful for detergent formulations, and their incorporation into such formulations, are disclosed in U.S. Pat. No. 4,261,868, Hora et al., issued Apr. 14, 1981. Enzymes for use in detergents can be stabilized by various techniques. Enzyme stabilization techniques are disclosed and exemplified in U.S. Pat. No. 4,261,868 issued Apr. 14, 1981, to Horn et al., U.S. Pat. No. 3,600,319 issued Aug. 17, 1971 to Gedge et al., and European Patent Application No. 0 199 405, Application No. 86200586.6, published Oct. 29, 1986, Venegas. Enzyme stabilization systems are also described for example, in U.S. Pat. Nos. 4,261,868; 3,600,319 and 3,519,570.

Enzyme Stabilizers

The enzymes employed herein can be stabilized by the presence of water-soluble sources of calcium and/or magnesium ions in the finished compositions which provide such ions to the enzymes. (Calcium ions are generally somewhat more effective than magnesium ions and are preferred herein if only one type of cation is being used). Additional stability can be provided by the presence of various other art-disclosed stabilizers, especially borate species: See Severson, U.S. Pat. No. 4,537,706, cited above. Typical detergents, especially liquids, will comprise from about 1 to about 30, preferably from about 2 to about 20, more preferably from about 5 to about 15, and most preferably from about 8 to about 12, millimoles of calcium ion per kilo of finished composition. This can vary somewhat, depending on the amount of enzyme present and its response to the calcium or magnesium ions. The level of calcium or magnesium ions should be selected so that there is always some minimum level available for the enzyme, after allowing for complexation with builders, fatty acids, etc., in the composition. Any water-soluble calcium or magnesium salt can be used as the source of calcium or magnesium ions, including, but not limited to, calcium chloride, calcium sulfate, calcium malate, calcium maleate, calcium hydroxide, calcium formate, and calcium acetate, and the corresponding magnesium salts. A small amount of calcium ion, generally from about 0.05 to about 0.4 millimoles per kilo, is often also present in the composition due to calcium in the enzyme slurry and formula water. In granular detergent compositions, the formulation may include a sufficient quantity of a water-soluble calcium ion source to provide such amounts in the laundry liquor. In the alternative, natural water hardness may suffice.

It is to be understood that the foregoing levels of calcium and/or magnesium ions are sufficient to provide enzyme stability. More calcium and/or magnesium ions can be added to the compositions to provide an additional measure of grease removal performance. Accordingly, the compositions herein may comprise from about 0.05% to about 2% by weight of a water-soluble source of calcium or magnesium ions, or both. The amount can vary, of course, with the amount and type of enzyme employed in the composition.

The compositions herein may also optionally, but preferably, contain various additional stabilizers, especially borate-type stabilizers. Typically, such stabilizers will be used at levels in the compositions from about 0.25% to about 10%, preferably from about 0.5% to about 5%, more preferably from about 0.75% to about 3%, by weight of boric acid or other borate compound capable of forming boric acid in the composition (calculated on the basis of boric acid). Boric acid is preferred, although other compounds such as boric oxide, borax and other alkali metal borates (e.g., sodium ortho-, meta- and pyroborate, and sodium pentaborate) are suitable. Substituted boric acids (e.g., phenylboronic acid, butane boronic acid, and p-bromo phenylboronic acid) can also be used in place of boric acid.

Polymeric Soil Release Agent

Any polymeric soil release agent known to those skilled in the art can optionally be employed in the compositions and processes of this invention. Polymeric soil release agents are characterized by having both hydrophilic segments, to hydrophilize the surface of hydrophobic fibers, such as polyester and nylon, and hydrophobic segments, to deposit upon hydrophobic fibers and remain adhered thereto through completion of washing and rinsing cycles and, thus, serve as an anchor for the hydrophilic segments. This can enable stains occurring subsequent to treatment with the soil release agent to be more easily cleaned in later washing procedures.

The polymeric soil release agents useful herein especially include those soil release agents having: (a) one or more nonionic hydrophile components consisting essentially of (i) polyoxyethylene segments with a degree of polymerization of at least 2, or (ii) oxypropylene or polyoxypropylene segments with a degree of polymerization of from 2 to 10, wherein said hydrophile segments does not encompass any oxypropylene unit unless it is bonded to adjacent moieties at each end by ether linkages, or (iii) a mixture of oxyalkylene units comprising oxyethylene and from 1 to about 30 oxypropylene units wherein said mixture contains a sufficient amount of oxyethylene units such that the hydrophile component has hydrophilicity great enough to increase the hydrophilicity of conventional polyester synthetic fiber surfaces upon deposit of the soil release agent on such surface, said hydrophile segments preferably comprising at least about 25% oxyethylene units and more preferably, especially for such components having about 20 to 30 oxypropylene units, at least about 50% oxyethylene units; or (b) one or more hydrophobe components comprising (i) $C_3$ oxyalkylene terephthalate segments, wherein, if said hydrophobe components also comprise oxyethylene terephthalate, the ratio of oxyethylene terephthalate: $C_3$ oxyalkylene terephthalate units is about 2:1 or lower, (ii) $C_4$–$C_6$ alkylene or oxy $C_4$–$C_6$ alkylene segments, or mixtures therein, (iii) poly(vinyl ester) segments, preferably poly(vinyl acetate), having a degree of polymerization of at least 2 or (iv) $C_1$–$C_4$ alkyl ether or $C_4$ hydroxyalkyl ether substituents, or mixtures therein, wherein said substituents are present in the form of $C_1$–$C_4$ alkyl ether or $C_4$ hydroxyalkyl ether cellulose derivatives, or mixture therein, and such cellulose derivatives are amphophilic, whereby they have a sufficient level of $C_1$–$C_4$ alkyl ether and/or $C_4$ hydroxyalkyl ether units to deposit upon conventional polyester synthetic fiber surfaces and retain a sufficient level of hydroxyls, once adhered to such conventional synthetic fiber surface, to increase fiber surface hydrophilicity, or a combination of (a) and (b).

Typically, the polyoxyethylene segments of (a)(i) will have a degree of polymerization of from 2 to about 200, although higher levels can be used, preferably from 3 to about 150, more preferably from 6 to about 100. Suitable oxy $C_4$–$C_6$ alkylene hydrophobe segments include, but are not limited to, end-caps of polymeric soil release agents such as $MO_3S(CH_2)_nOCH_2CH_2O$—, where M is sodium and n is an integer from 4–6, as disclosed in U.S. Pat. No. 4,721,580, issued Jan. 26, 1988, to Gosselink.

Polymeric soil release agents useful in the present invention also include cellulosic derivatives such as hydroxyether cellulosic polymers, copolymeric blocks of ethylene terephthalate or propylene terephthalate with polyethylene oxide or polypropylene oxide terephthalate, and the like. Such agents are commercially available and include hydroxyethers of cellulose such as METHOCEL (Dow). Cellulosic soil release agents for use herein also include those selected from the group consisting of $C_1$–$C_4$ alkyl and $C_4$ hydroxyalkyl cellulose; See U.S. Pat. No. 4,000,093, issued Dec. 28, 1976, to Nicol et al.

Soil release agents characterized by poly(vinyl ester) hydrophobe segments include graft copolymers of poly (vinyl ester), e.g., $C_1$–$C_6$ vinyl esters, preferably poly(vinyl acetate) grafted onto polyalkylene oxide backbones, such as polyethylene oxide backbones. See European Patent Application No. 0 219 048 published Apr. 22, 1987 by Kud et al. Commercially available soil release agents of this kind include the SOKALAN type of material, e.g., SOKALAN HP-22, available from BASF (West Germany).

One type of soil release agent is a copolymer having random blocks of ethylene terephthalate and polyethylene oxide (PEO) terephthalate. The molecular weight of this polymeric soil release agent is in the range of from about 25,000 to about 55,000. See U.S. Pat. No. 3,959,230 to Hays, issued May 25, 1976, and U.S. Pat. No. 3,893,929 to Basadur issued Jul. 8, 1975.

Another polymeric soil release agent is a polyester with repeat units of ethylene terephthalate units containing 10–15% by weight of ethylene terephthalate units together with 90–80% by weight of polyoxyethylene terephthalate units, derived from a polyoxyethylene glycol of average molecular weight 300–5,000. Examples of this polymer include the commercially available material ZELCON 5126 (from Dupont) and MILEASE T (from ICI). See also, U.S. Pat. No. 4,702,857, issued Oct. 27, 1987 to Gosselink.

Another polymeric soil release agent is a sulfonated product of a substantially linear ester oligomer comprised of an oligomeric ester backbone of terephthaloyl and oxyalkyleneoxy repeat units and terminal moieties covalently attached to the backbone. These soil release agents are described fully in U.S. Pat. No. 4,968,451, issued Nov. 6, 1990 to J. J. Scheibel and E. P. Gosselink.

Other suitable polymeric soil release agents include the terephthalate polyesters of U.S. Pat. No. 4,711,730 issued Dec. 8, 1987 to Gosselink et al., the anionic end-capped oligomeric esters of U.S. Pat. No. 4,721,580, issued Jan. 26, 1988 to Gosselink, and the block polyester oligomeric compounds of U.S. Pat. No. 4,702,857, issued Oct. 27, 1987 to Gosselink.

Still other polymeric soil release agents also include the soil release agents of U.S. Pat. No. 4,877,896, issued Oct. 31, 1989 to Maldonado et al., which discloses anionic, especially sulfoaroyl, end-capped terephthalate esters.

If utilized, soil release agents will generally comprise from about 0.01% to about 10.0% by weight, of the detergent compositions herein, typically from about 0.1% to about 5%, preferably from about 0.2% to about 3.0%.

Co-chelating Agents

The detergent compositions herein may also optionally contain one or more iron and/or manganese co-chelating agents. Such chelating agents can be selected from the group consisting of amino carboxylates, amino phosphonates, polyfunctionally-substituted aromatic chelating agents and mixtures therein, all as hereinafter defined. Without intending to be bound by theory, it is believed that the benefit of these materials is due in part to their exceptional ability to remove iron and manganese ions from washing solutions by formation of soluble chelates.

Amino carboxylates useful as optional chelating agents include ethylenediaminetetraacetates, N-hydroxyethylethylenediaminetriacetates, nitrilotriacetates, ethylenediamine tetrapropionates, triethylenetetraaminehexaacetates, diethylenetriaminepentaacetates, ethylenediaminedisuccinate, and ethanoldiglycines, alkali metal, ammonium, and substituted ammonium salts therein and mixtures therein.

Amino phosphonates are also suitable for use as chelating agents in the compositions of the invention when at least low levels of total phosphorus are permitted in detergent compositions, and include ethylenediaminetetrakis (methylenephosphonates), nitrilotris (methylenephosphonates) and diethylenetriaminepentakis (methylenephosphonates) as DEQUEST®. Preferably, these amino phosphonates do not contain alkyl or alkenyl groups with more than about 6 carbon atoms.

Polyfunctionally-substituted aromatic chelating agents are also useful in the compositions herein. See U.S. Pat. No. 3,812,044, issued May 21, 1974, to Connor et al. Preferred compounds of this type in acid form are dihydroxydisulfobenzenes such as 1,2-dihydroxy-3,5-disulfobenzene.

If utilized, these chelating agents will generally comprise from about 0.1% to about 10% by weight of the detergent compositions herein. More preferably, if utilized, the chelating agents will comprise from about 0.1% to about 3.0% by weight of such composition.

Clay Soil Removal/Anti-redeposition Agents

The compositions of the present invention can also optionally contain water soluble ethoxylated amines having clay soil removal and anti-redeposition properties. Granular detergent compositions which contain these compounds typically contain from about 0.01% to about 10.0% by weight of the water-soluble ethoxylated amines.

The most preferred soil release and anti-redeposition agent is ethoxylated tetraethylenepentamine. Exemplary ethoxylated amines are further described in U.S. Pat. No. 4,597,898, VanderMeer, issued Jul. 1, 1986. Another group of preferred clay soil removal/antiredeposition agents are the cationic compounds disclosed in European Patent Application 111 965, Oh and Gosselink, published Jun. 27, 1984.

Other clay soil removal/antiredeposition agents which can be used include the ethoxylated amine polymers disclosed in European Patent Application 111 984, Gosselink, published Jun. 27, 1984; the zwitterionic polymers disclosed in European Patent Application 112 592, Gosselink, published Jul. 4, 1984; and the amine oxides disclosed in U.S. Pat. No. 4,548,744, Connor, issued Oct. 22, 1985. Other clay soil removal and/or antiredeposition agents known in the art can also be utilized in the compositions herein. Another type of preferred antiredeposition agent includes the carboxymethyl cellulose (CMC) materials. These materials are well known in the art.

Polymeric Dispersing Agents

Polymeric dispersing agents can advantageously be utilized at levels from about 0.1% to about 7%, by weight in the compositions herein, especially in the presence of zeolite and/or layered silicate builders. Suitable polymeric dispersing agents include polymeric polycarboxylates and polyethylene glycols, although others known in the art can also be used. It is believed, though it is not intended to be limited by theory, that polymeric dispersing agents enhance overall detergent builder performance, when used in combination with other builders (including lower molecular weight polycarboxylates) by crystal growth inhibition, particulate soil release peptization, and anti-redeposition.

Polymeric polycarboxylate materials can be prepared by polymerizing or copolymerizing suitable unsaturated monomers, preferably in their acid form. Unsaturated monomeric acids that can be polymerized to form suitable polymeric polycarboxylates include acrylic acid, maleic acid (or maleic anhydride), fumaric acid, itaconic acid, aconitic acid, mesaconic acid, citraconic acid and methylenemalonic acid. The presence in the polymeric polycarboxylates herein of monomeric segments, containing no carboxylate radicals such as vinylmethyl ether, styrene, ethylene, etc., is suitable provided that such segments do not constitute more than about 40% by weight.

Particularly suitable polymeric polycarboxylates can be derived from acrylic acid. Such acrylic acid-based polymers which are useful herein are the water-soluble salts of polymerized acrylic acid. The average molecular weight of such polymers in the acid form preferably ranges from about 2,000 to 10,000, more preferably from about 4,000 to 7,000 and most preferably from about 4,000 to 5,000. Water-soluble salts of such acrylic acid polymers can include, for example, the alkali metal, ammonium and substituted ammonium salts. Soluble polymers of this type are known materials. Use of polyacrylates of this type in detergent compositions has been disclosed, for example, in Diehl, U.S. Pat. No. 3,308,067, issued Mar. 7, 1967.

Acrylic/maleic-based copolymers may also be used as a preferred component of the dispersing/anti-redeposition agent. Such materials include the water-soluble salts of copolymers of acrylic acid and maleic acid. The average molecular weight of such copolymers in the acid form preferably ranges from about 2,000 to 100,000, more preferably from about 5,000 to 75,000, most preferably from about 7,000 to 65,000. The ratio of acrylate to maleate segments in such copolymers will generally range from about 30:1 to about 1:1, more preferably from about 10:1 to 2:1. Water-solute salts of such acrylic acid/maleic acid copolymers can include, for example, the alkali metal, ammonium and substituted ammonium salts. Soluble acrylate/maleate copolymers of this type are known materials which are described in European Patent Application No. 66 915, published Dec. 15, 1982.

Another polymeric material which can be included is polyethylene glycol (PEG). PEG can exhibit dispersing agent performance as well as act as a clay soil removal/antiredeposition agent. Typical molecular weight ranges for these purposes range from about 500 to about 100,000, preferably from about 1,000 to about 50,000, more preferably from about 1,500 to about 10,000.

Polyaspartate and polyglutamate dispersing agents may also be used, especially in conjunction with zeolite builders.

Brightener

Any optical brighteners or other brightening or whitening agents known in the art can be incorporated at levels typically from about 0.05% to about 1.2% by weight, into the detergent compositions herein. Commercial optical brighteners which may be useful in the present invention can be classified into subgroups which include, but are not necessarily limited to, derivatives of stilbene, pyrazoline, coumarin, carboxylic acid, methinecyanines, dibenzothiphene-5,5-dioxide, azoles, 5- and 6-membered-ring heterocycles, and other miscellaneous agents. Examples of such brighteners are disclosed in "The Production and Application of Fluorescent Brightening Agents", M. Zahradnik, Published by John Wiley & Sons, New York (1982).

Specific examples of optical brighteners which are useful in the present compositions are those identified in U.S. Pat. No. 4,790,856, issued to Wixon on Dec. 13, 1988. These brighteners include the PHORWHITE series of brighteners from Verona. Other brighteners disclosed in this reference include: Tinopal UNPA, Tinopal CBS and Tinopal 5BM; available from Ciba-Geigy; Arctic White CC and Artic White CWD, available from Hilton-Davis, located in Italy; the 2-(4-styrylphenyl)-2H-naphthol[1,2-d]triazoles; 4,4'-bis' (1,2,3-triazol-2-yl)stilbenes; 4,4'-bis(styryl)bisphenyls; and the aminocoumarins. Specific examples of these brighteners include 4-methyl-7-diethylaminocoumarin; 1,2-bis(benzimidazol-2-yl)ethylene; 1,3-diphenylphrazolines; 2,5-bis(benzoxazol-2-yl)thiophene; 2-styrylnaphth[1,2-d]oxazole; and 2-(stilbene-4-yl-2H-naphtho[1,2-d]triazole. See also U.S. Pat. No. 3,646,015, issued Feb. 29, 1972, to Hamilton which is incorporated herein by reference.

Suds Suppressors

Compounds for reducing or suppressing the formation of suds can be incorporated into the compositions of the present invention. Suds suppression can be of particular importance under conditions such as those found in European-style front loading laundry washing machines, or in the concentrated detergency process of U.S. Pat. Nos. 4,489,455 and 4,478,574, or when the detergent compositions herein optionally include a relatively high sudsing adjunct surfactant.

A wide variety of materials may be used as suds suppressors, and suds suppressors are well known to those skilled in the art. See, for example, Kirk Othmer Encyclopedia of Chemical Technology, Third Edition, Volume 7, pages 430–447 (John Wiley & Sons, Inc., 1979). One category of suds suppressor of particular interest encompasses monocarboxylic fatty acids and soluble salts therein. See U.S. Pat. No. 2,954,347, issued Sep. 27, 1960 to Wayne St. John. The monocarboxylic fatty acids and salts thereof used as suds suppressor typically have hydrocarbyl chains of 10 to about 24 carbon atoms, preferably 12 to 18 carbon atoms. Suitable salts include the alkali metal salts such as sodium, potassium, and lithium salts, and ammonium and alkanolammonium salts.

The detergent compositions herein may also contain non-surfactant suds suppressors. These include, for example: high molecular weight hydrocarbons such as paraffin, fatty acid esters (e.g., fatty acid triglycerides), fatty acid esters of monovalent alcohols, aliphatic $C_{18}$–$C_{40}$ ketones (e.g., stearone), etc. Other suds inhibitors include N-alkylated amino triazines such as tri- to hexa-alkylmelamines or di- to tetraalkyldiamine chlortriazines formed as products of cyanuric chloride with two or three moles of a primary or secondary amine containing 1 to 24 carbon atoms, propylene oxide, and monostearyl phosphates such as monostearyl alcohol phosphate ester and monostearyl di-alkali metal (e.g., K, Na, and Li) phosphates and phosphate esters. The hydrocarbons such as paraffin and haloparaffin can be utilized in liquid form. The liquid hydrocarbons will be liquid at room temperature and atmospheric pressure, and will have a pour point in the range of about −40° C. and about 5° C., and a minimum boiling point not less than about 110° C. (atmospheric pressure). It is also known to utilize waxy hydrocarbons, preferably having a melting point below about 100° C. The hydrocarbons constitute a preferred category of suds suppressor for detergent compositions. Hydrocarbon suds suppressors are described, for example, in U.S. Pat. No. 4,265,779, issued May 5, 1981 to Gandolfo et al. The hydrocarbons, thus, include aliphatic, alicyclic, aromatic, and heterocyclic saturated or unsaturated hydrocarbons having from about 12 to about 70 carbon atoms. The term "paraffin", as used in this suds suppressor discussion, is intended to include mixtures of true paraffins and cyclic hydrocarbons.

Another preferred category of non-surfactant suds suppressors comprises silicone suds suppressors. This category includes the use of polyorganosiloxane oils, such as polydimethylsiloxane, dispersions or emulsions of polyorganosiloxane oils or resins, and combinations of polyorganosiloxane with silica particles wherein the polyorganosiloxane is chemisorbed or fused onto the silica. Silicone suds suppressors are well known in the art and are, for example, disclosed in U.S. Pat. No. 4,265,779, issued May 5, 1981 to Gandolfo et al. and European Patent Application No. 89307851.9, published Feb. 7, 1990 by Starch, M. S.

Other silicone suds suppressors are disclosed in U.S. Pat. 3,455,839 which relates to compositions and processes for defoaming aqueous solutions by incorporating therein small amounts of polydimethylsiloxane fluids.

Mixtures of silicone and silanated silica are described, for instance, in German Patent Application DOS 2,124,526. Silicone defoamers and suds controlling agents in granular detergent compositions are disclosed in U.S. Pat. No. 3,933,672, Bartolotta et al., and in U.S. Pat. No. 4,652,392, Baginski et al., issued Mar. 24, 1987.

An exemplary silicone based suds suppressor for use herein is a suds suppressing amount of a suds controlling agent consisting essentially of:

(i) polydimethylsiloxane fluid having a viscosity of from about 20 cs. to about 1500 cs at 25° C.;

(ii) from about 5 to about 50 parts per 100 parts by weight of (i) of siloxane resin composed of $(CH_3)_3SiO_{1/2}$ units of $SiO_2$ units in a ratio of from $(CH_3)_3SiO_{1/2}$ units and to $SiO_2$ units of from about 0.6:1 to about 1.2:1; and (iii) from about 1 to about 20 parts per 100 parts by weight of (i) of a solid silica gel.

In the preferred silicone suds suppressor used herein, the solvent for a continuous phase is made up of certain polyethylene glycols or polyethylene-polypropylene glycol copolymers or mixtures thereof (preferred), and not polypropylene glycol. The primary silicone suds suppressor is branched/crosslinked and not linear.

To illustrate this point further, typical laundry detergent compositions with controlled suds will optionally comprise from about 0.001 to about 1, preferably from about 0.01 to about 0.7, most preferably from about 0.05 to about 0.5 weight % of said silicone suds suppressor, which comprises (1) a nonaqueous emulsion of a primary antifoam agent which is a mixture of (a) a polyorganosiloxane, (b) a resinous siloxane or a silicone resin-producing silicone compound, (c) a finely divided filler material, and (c), to form silanolates; (2) at least one nonionic silicone surfactant; and (3) polyethylene glycol or a copolymer of polyethylene-polypropylene glycol having a solubility in water at room temperature of more than about 2 weight %; and without polypropylene glycol. Similar amounts can be used in granular compositions, gels, etc. See also U.S. Pat. No. 4,978,471, Starch, issued Dec. 18, 1990; and U.S. Pat. No. 4,983,316, Starch, issued Jan. 8, 1991; and U.S. Pat. Nos. 4,639,489 and 4,749,740, Aizawa et al. at column 1, line 46 through column 4, line 35.

The silicone suds suppressor herein preferably comprises polyethylene glycol and a copolymer of polyethylene glycol/polypropylene glycol, all having an average molecular weight of less than about 1,000, preferably between about 100 and 800. The polyethylene glycol and polyethylene/polypropylene copolymers herein have a solubility in water at room temperature of more than about 2 weight %, preferably more than about 5 weight %.

The preferred solvent herein is polyethylene glycol having an average molecular weight of less than about 1,000, more preferably between about 100 and 800, most preferably between 200 and 400, and a copolymer of polyethylene glycol/polypropylene glycol, preferably PPG 200/PEG 300. Preferred is a weight ratio of between about 1:1 and 1:10, most preferably between 1:3 and 1:6, of polyethylene glycol:copolymer of polyethylene-polypropylene glycol.

The preferred silicone suds suppressors used herein do not contain polypropylene glycol, particularly of 4,000 molecular weight. They also preferably do not contain block copolymers of ethylene oxide and propylene oxide, like PLURONIC L101.

Other suds suppressors useful herein comprise the secondary alcohols (e.g., 2-alkyl alkanols) and mixtures of such alcohols with silicone oils, such as the silicones disclosed in U.S. Pat. Nos. 4,798,679; 4,075,118 and EP 150 872. The secondary alcohols include the $C_6$–$C_{16}$ alkyl alcohols having a $C_1$–$C_{16}$ chain. A preferred alcohol is 2-butyl octanol, which is available from Condea under the trademark ISOFOL 12. Mixtures of secondary alcohols are available under the trademark ISALCHEM 123 from Enichem. Mixed suds suppressors typically comprise mixtures of alcohol+silicone at a weight ratio of 1:5 to 5:1.

For any detergent compositions to be used in automatic laundry washing machines, suds should not form to the extent that they overflow the washing machine. Suds suppressors, when utilized, are preferably present in a "suds suppressing amount". By "suds suppressing amount" is meant that the formulator of the composition can select an amount of this suds controlling agent that will sufficiently control the suds to result in a low-sudsing laundry detergent for use in automatic laundry washing machines.

The compositions herein will generally comprise from 0% to about 5% of suds suppressor. When utilized as suds suppressors, monocarboxylic fatty acids, and salts therein, will be present typically in amounts up to about 5%, by weight, of the detergent composition. Preferably, from about 0.5% to about 3% of fatty monocarboxylate suds suppressor is utilized. Silicone suds suppressors are typically utilized in amounts up to about 2.0%, by weight, of the detergent composition, although higher amounts may be used. This upper limit is practical in nature, due primarily to concern with keeping costs minimized and effectiveness of lower amounts for effectively controlling sudsing. Preferably from about 0.01% to about 1% of silicone suds suppressor is used, more preferably from about 0.25% to about 0.5%. As used herein, these weight percentage values include any silica that may be utilized in combination with polyorganosiloxane, as well as any adjunct materials that may be utilized. Monostearyl phosphate suds suppressors are generally utilized in amounts ranging from about 0.1% to about 2% by weight of the composition. Hydrocarbon suds suppressors are typically utilized in amounts ranging from about 0.01% to about 5.0%, although higher levels can be used. The alcohol suds suppressors are typically used at 0.2%–3% by weight of the finished compositions.

In addition to the foregoing ingredients, the compositions herein can also be used with a variety of other adjunct ingredients which provide still other benefits in various compositions within the scope of this invention. The following illustrates a variety of such adjunct ingredients, but is not intended to be limiting therein.

Fabric Softeners

Various through-the-wash fabric softeners, especially the impalpable smectite clays of U.S. Pat. No. 4,062,647, Storm and Nirschl, issued Dec. 13, 1977, as well as other softener clays known in the art, can optionally be used typically at levels of from about 0.5% to about 10% by weight in the present compositions to provide fabric softener benefits concurrently with the fabric cleaning. Clay softeners can be used in combination with amine and cationic softeners, as disclosed, for example, in U.S. Pat. No. 4,375,416, Crisp et al., Mar. 1, 1983, and U.S. Pat. No. 4,291,071, Harris et al., issued Sep. 22, 1981. Mixtures of cellulase enzymes (e.g., CAREZYME, Novo) and clays are also useful as high-performance fabric softeners. Various cationic materials can be added to enhance static control.

Dye Transfer Inhibiting Agents

The compositions of the present invention may also include one or more materials effective for inhibiting the transfer of dyes from one fabric to another during the cleaning process. Generally, such dye transfer inhibiting agents include polyvinyl pyrrolidone polymers, polyamine N-oxide polymers, copolymers of N-vinylpyrrolidone and N-vinylimidazole, manganese phthalocyanine, peroxidases, and mixtures thereof. If used, these agents typically comprise from about 0.01% to about 10% by weight of the composition, preferably from about 0.01% to about 5%, and more preferably from about 0.05% to about 2%.

More specifically, the polyamine N-oxide polymers preferred for use herein contain units having the following structural formula: R—$A_x$—P; wherein P is a polymerizable unit to which an N—O group can be attached or the N—O group can form part of the polymerizable unit or the N—O group can be attached to both units; A is one of the following structure: —NC(O)—, —C(O)O—, —S—, —O—, —N=; x is 0 or 1; and R is aliphatic, ethoxylated aliphatics, aromatics, heterocyclic or alicyclic groups or any combination thereof to which the nitrogen of the N—O group can be attached or the N—O group is part of these groups. Preferred polyamine N-oxides are those wherein R is a heterocyclic group such as pyridine, pyrrole, imidazole, pyrrolidine, piperidine and derivatives thereof.

The N—O group can be represented by the following general structures:

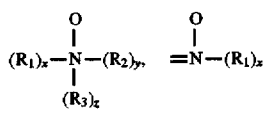

wherein $R_1$, $R_2$, $R_3$ are aliphatic, aromatic, heterocyclic or alicyclic groups or combinations thereof; x, y and z are 0 or 1; and the nitrogen of the N—O group can be attached or form part of any of the aforementioned groups. The amine oxide unit of the polyamine N-oxides has a pKa<10, preferably pKa<7, more preferred pKa<6.

Any polymer backbone can be used as long as the amine oxide polymer formed is water-soluble and has dye transfer inhibiting properties. Examples of suitable polymeric backbones are polyvinyls, polyalkylenes, polyesters, polyethers, polyamide, polyimides, polyacrylates and mixtures thereof. These polymers include random or block copolymers where one monomer type is an amine N-oxide and the other monomer type is an N-oxide. The amine N-oxide polymers typically have a ratio of amine to the amine N-oxide of 10:1 to 1:1,000,000. However, the number of amine oxide groups present in the polyamine oxide polymer can be varied by appropriate copolymerization or by an appropriate degree of N-oxidation. The polyamine oxides can be obtained in almost any degree of polymerization. Typically, the average molecular weight is within the range of 500 to 1,000,000; more preferred 1,000 to 500,000; most preferred 5,000 to 100,000. This preferred class of materials can be referred to as "PVNO".

The most preferred polyamine N-oxide useful in the detergent compositions herein is poly(4-vinylpyridine-N-oxide) which has an average molecular weight of about 50,000 and an amine to amine N-oxide ratio of about 1:4.

Copolymers of N-vinylpyrrolidone and N-vinylimidazole polymers (referred to as a class as "PVPVI") are also preferred for use herein. Preferably the PVPVI has an average molecular weight range from 5,000 to 1,000,000, more preferably from 5,000 to 200,000, and most preferably from 10,000 to 20,000. (The average molecular weight range is determined by light scattering as described in Barth et al., Chemical Analysis, Vol. 113, "Modern Methods of POlymer Characterization", the disclosures of which are incorporated herein by reference). The PVPVI copolymers typically have a molar ratio of N-vinylimidazole to N-vinylpyrrolidone from 1:1 to 0.2:1, more preferably from 0.8:1 to 0.3:1, most preferably from 0.61 to 0.4:1. There copolymers can be either linear or branched.

The present invention compositions also may employ a polyvinylpyrrolidone ("PVP") having an average molecular weight of from about 5,000 to about 400,000, preferably from about 5,000 to about 200,000, and more preferably from about 5,000 to about 50,000. PVP's are known to persons skilled in the detergent field; see, for example, EP-A-262,897 and EP-A-256,696, incorporated herein by reference. Compositions containing PVP can also contain polyethylene glycol ("PEG") having an average molecular weight from about 500 to about 100,000, preferably from about 1,000 to about 10,000. Preferably, the ratio of PEG to PVP on a ppm basis delivered in wash solutions is from about 2:1 to about 50:1, and more preferably from about 3:1 to about 10:1.

The detergent compositions herein may also optionally contain from about 0.005% to 5% by weight of certain types of hydrophilic optical brighteners which also provide a dye transfer inhibition action. If used, the compositions herein will preferably comprise from about 0.01% to 1% by weight of such optical brighteners.

The hydrophilic optical brighteners useful in the present invention are those having the structural formula:

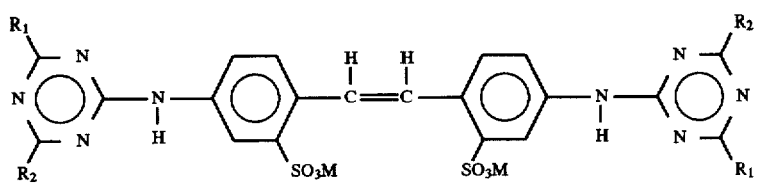

wherein $R_1$ is selected from anilino, N-2-bis-hydroxyethyl and NH-2-hydroxyethyl; $R_2$ is selected from N-2-bis-hydroxyethyl, N-2-hydroxyethyl-N-methylamino, morpholino, chloro and amino; and M is a salt-forming cation such as sodium or potassium.

When in the above formula, $R_1$ is anilino, $R_2$ is N-2-bis-hydroxyethyl and M is a cation such as sodium, the brightener is 4,4'-bis[(4-anilino-6-(N-2-bis-hydroxy-ethyl)-s-triazine-2-yl)amino]-2,2'-stilbenedisulfonic acid and disodium salt. This particular brightener species is commercially marketed under the tradename Tinopai-UNPA-GX by Ciba-Geigy Corporation. TinopaI-UNPA-GX is the preferred hydrophilic optical brightener useful in the detergent compositions herein.

When in the above formula, $R_1$ is anilino, $R_2$ is N-2-hydroxyethyl-N-2-methylamino and M is a cation such as sodium, the brightener is 4,4'-bis[(4-anilino-6-(N-2-hydroxyethyl-N-methylamino)-s-triazine-2-yl)amino]-2,2'-stilbenedisulfonic acid disodium salt. This particular brightener species is commercially marketed under the tradename Tinopal 5BM-GX by Ciba-Geigy Corporation.

When in the above formula, $R_1$ is anilino, $R_2$ is morphilino and M is a cation such as sodium, the brightener is 4,4'-bis[(4-anilino-6-morphilino-s-triazine-2-yl)amino]-2,2'-stilbenedisulfonic acid, sodium salt. This particular brightener species is commercially marketed under the tradename Tinopal AMS-GX by Ciba Geigy Corporation.

The specific optical brightener species selected for use in the present invention provide especially effective dye transfer inhibition performance benefits when used in combination with the selected polymeric dye transfer inhibiting agents hereinbefore described. The combination of such selected polymeric materials (e.g., PVNO and/or PVPVI) with such selected optical brighteners (e.g., Tinopal UNPA-GX, Tinopal 5BM-GX and/or Tinopal AMS-GX) provides significantly better dye transfer inhibition in aqueous wash solutions than does either of these two detergent composition components when used alone.

The detergent compositions of the present invention are optionally substantially free of any peroxygen compounds. As used herein, "substantially free" means that the detergent compositions contain less than about 0.01%, preferably less than about 0.005%, by weight of a peroxygen compound. Examples of peroxygen compounds commonly used in bleaching solutions include hydrogen peroxide and its derivatives, such as alkali metal peroxides and superoxides, perborates, persulfates; and peracids, such as persulfonic acid, peracetic acid, peroxy monophosphoric acid and their water-soluble salts, especially their alkali metal, ammonium or organic amine salts; and urea-hydrogen peroxide addition product.

Other Ingredients

Other additional optional ingredients which can be present in detergent compositions of the invention (in their conventional art-established levels for use generally from 0.001% to about 50% by weight of the detergent composition), include solvents, hydrotropes, solubilizing agents, processing aids, soil-suspending agents, corrosion inhibitors, dyes, fillers, carriers, germicides, pH-adjusting agents, perfumes, static control agents, thickening agents, abrasive agents, viscosity control agents, solubilizing/clarifying agents, sunscreens/UV absorbers, phase regulants, foam boosting/stabilizing agents, antioxidants, metal ions, buffering agents, color speckles, encapsulation agents, deflocculating polymers, skin protective agents, color care agents, bleaching agents, bleach activators, bleach stabilizers, bleach catalysts and the like.

Various detersive ingredients employed in the present compositions optionally can be further stabilized by absorbing said ingredients onto a porous hydrophobic substrate, then coating said substrate with a hydrophobic coating. Preferably, the detersive ingredient is admixed with a surfactant before being absorbed into the porous substrate. In use, the detersive ingredient is released from the substrate into the aqueous washing liquor, where it performs its intended detersive function.

To illustrate this technique in more detail, a porous hydrophobic silica (trademark SIPERNAT D10, DeGussa) is admixed with a proteolytic enzyme solution containing 3%–5% of $C_{13-15}$ ethoxylated alcohol EO(7)$_n$ nonionic surfactant. Typically, the enzyme/surfactant solution is 2.5× the weight of silica. The resulting powder is dispersed with stirring in silicone oil (various silicone oil viscosities in the range of 500–12,500 can be used). The resulting silicone oil dispersion is emulsified or otherwise added to the final detergent matrix. By this means, ingredients such as the aforementioned enzymes, bleaches, bleach activators, bleach catalysts, photoactivators, dyes, fluorescers, fabric conditioners and hydrolyzable surfactants can be "protected" for use in detergents, including liquid laundry detergent compositions.

Many additional essential and optional ingredients that are useful in the present invention are those described in McCutcheon's, *Detergents and Emulsifiers* (Vol. 1) and McCutcheon's, *Functional Materials* (Vol. 2), 1995 Annual Edition, published by McCutcheon's MC Publishing Co., as well as the CTFA (Cosmetic, Toiletry and Fragrance Association)1992 International Buyers Guide, published by CFTA Publications and OPD 1993 Chemicals Buyers Directory 80th Annual Edition, published by Schnell Publishing Co. which are all incorporated herein by reference.

Powdered detergent composition might contain the following by weight:

(1) 1–75% detergent surfactant system;
(2) 5–80% builder;
(3) 0–30% buffer salt;
(4) 0–30% sulfate;
(5) 0–4% enzyme;
(6) 0.1–50% hydroxy containing alkyl glycamides;
(7) 0–40% bleach system;
(8) water and additional optional ingredients to 100%.

A preferred powdered detergent composition might contain the following by weight:

(1) 5–60% detergent surfactant system;
(2) 10–50% builder;
(3) 0–28% buffer salt;
(4) 0–28% sulfate;
(5) 0–3.5% enzyme;
(6) 0.2–25% hydroxy containing alkyl glycamide;
(7) 0–30% bleach system;
(8) water and additional optional ingredients to 100%.

A liquid detergent composition might contain the following by weight:

(1) 1–75% detergent surfactant system;
(2) 5–80% builder;
(3) 0–40% electrolyte;
(4) 0–5% enzyme;
(5) 0–15% enzyme stabilizer;
(6) 0–20% phase regulant;
(7) 0.1–50% hydroxy containing alkyl glycamides;
(8) water and additional optional ingredients to 100%.

A preferred liquid detergent composition might contain the following by weight:

(1) 5–60% detergent surfactant system;
(2) 7–30% builder;
(3) 0–30% electrolyte;
(4) 0.01–4% enzyme;
(5) 0.01–14% enzyme stabilizer;
(6) 0–18% phase regulant;
(7) 0.2–25% hydroxy containing alkyl glycamides;
(8) water and additional optional ingredients to 100%.

Detergent Formulations

Granular detergent compositions embodying the present invention can be formed by conventional techniques, i.e., by slurring the individual components in water and then atomizing and spray-drying the resultant mixtures, or by pan or drum agglomeration of the ingredients. Granular formulations preferably comprise from about 5% to about 60% of detergent surfactant selected from the group consisting of anionic surfactants, nonionic surfactants, and mixtures thereof.

Liquid compositions of the present invention can contain water and other solvents. Lower molecular weight primary or secondary alcohols, exemplified by methanol, ethanol, propanol, and isopropanol, are suitable. Monohydric alcohols are preferred for solubilizing the surfactant, but polyols containing from about 2 to about 6 carbon atoms and from about 2 to about 6 hydroxy groups can be used and can provide improved enzyme stability (if enzymes are included in the composition). Examples of polyols include propylene glycol, ethylene glycol, glycerine and 1,2 propanediol. Ethanol is a particularly preferred alcohol.

The liquid compositions preferably comprise from about 5% to about 60% of detergent surfactant, about 7% to about 30% of builder and about 0.2% to about 25% hydroxy containing alkyl glycamide surfactant.

Useful detergency builders in liquid compositions include the alkali metal silicates, alkali metal carbonates, polyphosphonic acids, $C_{10}$–$C_{18}$ alkyl monocarboxylic acids, polycarboxylic acids, alkali metal, ammonium or substituted ammonium salts thereof, and mixtures thereof. In preferred liquid compositions, from about 8% to about 28% of the detergency builders are selected from the group consisting of $C_{10}$–$C_{18}$ alkyl monocarboxylic acids, polycarboxylic acids and mixtures thereof.

Particularly, preferred liquid compositions contain from about 8% to about 18% of a $C_{10}$–$C_{18}$ monocarboxylic (fatty) acid and from about 0.2% to about 10% of a polycarboxylic acid, preferably citric acid, and provide a solution pH of from about 6 to about 10 at 1.0% concentration in water.

Preferred liquid compositions are substantially free of inorganic phosphates or phosphonates. As used in this context "substantially free" means that the liquid compositions contain less than about 0.5% by weight of an inorganic phosphate- or phosphonate-containing compound.

The detergent compositions of the invention are particularly suitable for laundry use, but are also suitable for the cleaning of hard surfaces and for dishwashing.

In a laundry method aspect of the invention, typical laundry wash water solutions comprise from about 100 ppm to about 5% by weight of the detergent compositions of the invention. Fabrics to be laundered are agitated in these solutions to effect cleaning and stain removal.

The detergent compositions of the present invention may be in any of the usual physical forms, such as powders, beads, flakes, bars, tablets, noodles, liquids, pastes and the like. The detergent compositions are prepared and utilized in the conventional manner. The wash solutions thereof desirably have a pH from about 6 to about 12, preferably from about 7 to about 11, more preferably from about 7.5 to about 8.5.

Method of Manufacture

In another embodiment of the invention a new process for the manufacture of hydroxy containing alkyl glycamide surfactants is described.

It has been found, in accordance with the present invention, that (I) novel hydroxy containing glycamide surfactants may be readily prepared by reacting alkyl lactones with glycamines in the presence of a basic catalyst but in the absence or presence of an organic solvent at elevated temperatures.

It has been further found, in accordance with the present invention, that (II) novel hydroxy containing glycamide surfactants may be readily prepared by reacting hydroxy containing fatty acid esters in the presence of base catalyst but in the absence or presence of an organic solvent at elevated temperatures.

The invention can be more readily understood when reference is made to the equations:

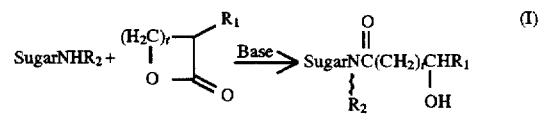

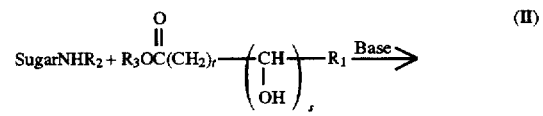

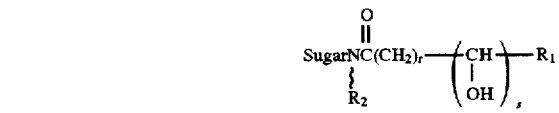

wherein $R_1$, $R_2$, $R_3$, t and s are defined as above

Examples of glycamines (1-amino-1-deoxyalditols, 2-amino-2-deoxyketitols, 1-alkylamino-1-deoxyalditols etc.) suitable for this method include those of the formula:

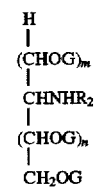

wherein G is hydrogen (H), $(CH_2CH_2O)_aH$ or a $(CH_2CHCH_3O)_bH$ group, a mono-, di-, oligo- or polysaccharide or mixtures thereof; a and b are each from about 0 to about 35 and the sum of a and b are from about 0 to about 35 and the sum of a and b are from about 0 to about 35; n is from about 1 to about 6, m is from about 0 to about 8 and the sum of n and m are from about 0 to about 10; and $R_2$ is hydrogen (H), a straight or branched chain saturated or unsaturated hydrocarbon which may be unsubstituted or substituted with a hydroxyl, polyhydroxyl, aromatic, cycloaliphatic or mixed aromatic radical having about 1 to about 31 carbon atoms.

Illustrative of this class include, but are not limited to glyceramine, erythramine, threamine, ribamine, arabinamine, xylamine, lyxamine, allamine, altramine, glucamine (1-amino-1-deoxyglucitol), mannamine, gulamine, idamine, galactamine, talamine, glucoheptamine (1-amino-1-deoxyglucoheptitol), 1-amino-1-deoxyglyceroglucoheptitol, 1-amino-1-deoxyglycergalactoheptitol, 1-amino-1-deoxyglyceromannoheptitol, 1,3-dihydroxy-2-propylamine, erythrulamine (threulamine or glycerotetrulamine), ribulamine (erythropentulamine), xylulamine (threopentulamine), psicamine, fructamine (levulamine or 2-amino-2-deoxyfructitol), sorbamine (2-amino-2-deoxysorbitol), tagatamine, 2-amino-2-deoxyalloheptulitol, 3-amino-3-deoxyaltro-3-heptulitol, 2-amino-2-deoxymannoheptulitol, 2-amino-2-deoxysedoheptulitol, 2-amino-2-deoxytaloheptulitol, 2-amino-2-deoxylcerogalactooctulitol, 2-amino-2-deoxyglyceromannooctulitol, 2-amino-2-deoxyerythrogalactononulitol, 2-amino-2-deoxyerythroglucononulitol, lactamine[galactopyranosyl-β-(1-4)-1-amino-1-deoxyglucitol], maltamine [glucopyranosyl-α-(1-4)-1-amino-1-deoxyglucitol], isomaltamine-A[glucopyranosyl-α-(1-6)-1-amino-1-deoxyglucitol], isomaltamine-B[glucopyranosyl-α-(1-6)-2-amino-2-deoxyfructitol], isomaltulamine[palatinamine or glucopyranosyl-α-(1-6)-2-amino-2-deoxyfructitol], cellobiamine[glucopyranosyl-β-(1-4)-1-amino-1-deoxyglucitol], leucramine[glucopranosyl-α-(1-5)-2-amino-2-deoxyfructitol], gentiobiamine[glucopyranosyl-β-(1-6)-1-amino-1-deoxyglucitol], laminarbiamine [glucopyranosyl-β-(1-3)-1-amino-1-deoxyglucitol], xylobiamine[xylopyranosyl-β-(1-4)-1-amino-1-deoxyxylitol], inulobiamine[fructopyranosyl-β-(2-1)-2-amino-2-deoxyfructitol], mannobiamine[mannopyranosyl-β-(1-4)-1-amino-1-deoxymannitol], 3-ketopalatinamine[3-ketoglucopyranosyl-α-(1-6)-2-amino-2-deoxyfructitol], arabinofuranosyl-β-(1-3)-1-amino-1-deoxyarabinitol, galactopyranosyl-α-(1-3)-1-amino-1-deoxygalactitol, maltotriamine[glucopyranosyl-α-(1-4)-glucopyranosyl-α-(1-4)-1-amino-1-deoxy-glucitol], cellotriamine [glucopyranosyl-β-(1-4)-glucopyranosyl-β-(1-4)-1-amino-1-deoxyglucitol], panosamine[glucopyranosyl-α-(1-6)-glucopyranosyl-β-(1-4)-1-amino-1-deoxyglucitol], maltoheptamine[glucopyranosyl-α-(1-4)-{glucopyranosyl-α-(1-4)}₅-1-amino-1-deoxyglucitol], starchamine, dextramine, cellulamine, 2-amino-2-deoxyglucitol(2-amino-2-deoxysorbitol), 3-amino-3-deoxyglucitol, 4-amino-4-deoxyglucitol, 6-amino-6-deoxyglucitol, 3-amino-3-deoxyribitol, 2-amino-2-deoxygalactitol, 2-amino-2-deoxymannitol, 2-amino-2-deoxyallitol, 5-amino-5-deoxyaltritol, 6-amino-6-deoxyerythrogalactooctitol, methylglucamine(1-methylamine-1-deoxyglucitol or 1-methylamine-1-deoxysorbitol), ethylglucamine, propylglucamine, butylglucamine, hydroxyethylglucamine, coconutglucamine, disorbitylamine, methyllactamine [galactopyranosyl-β-(1-4)-1-methylamino-1-deoxyglucitol], methylmaltamine[glucopyranosyl-β-(1-4)-1-methylamino-1-deoxyglucitol], ethyllactamine, propyllactamine, butyllactamine, hydroxyethyllactamine, coconutlactamine, ethylmaltamine, propyimaltamine, butylmaltamine, coconutmaltamine, pentylmaltamine, methyloxypropylglucamine, methyloxypropyllactamine, methyloxypropylmaitamine and $C_2$–$C_{18}$ oxypropylglucamine.

Examples of other glycamines (1-amino-1,6-dideoxyalditols and 1-alkylamino-1,6-dideoxyalditols) suitable for this method include those of the formula:

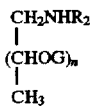

wherein G is hydrogen (H), a $(CH_2CH_2O)_aH$ or $(CH_2CHCH_3O)_bH$ group, a mono-, di-, oligo- or polysaccharide or mixtures thereof; a and b are each from about 0 to about 35 and the sum of a and b are from about 0 to about 35; n is from about 1 to about 6, m is from about 0 to about 8 and the sum of n and m are from about 0 to about 10; and $R_2$ is hydrogen (H), a straight or branched chain saturated or unsaturated hydrocarbon which may be unsubstituted or substituted with a hydroxyl, polyhydroxyl, aromatic, cycloaliphatic or mixed aromatic radical having about 1 to about 31 carbon atoms. Illustrative of this class include, but are not limited to 1-amino-1,6-dideoxyallitol, 1-amino-1,6-dideoxyaltritol, 1-amino-1,6-dideoxyglucitol, 1-amino-1,6-dideoxygulitol, 1-amino-1,6-di-deoxyalitol, 1-amino-1,6-dideoxyfucitol, 1-amino-1,6-dideoxyrhamnitol, 1-methylamino-1,6-dideoxyrhamnitol, 1-ethylamino-1,6,dideoxyrhamnitol, 1-coconutamino-1,6-dideoxyrhamnitol, 1-methyloxypropylamino-1,6-dideoxyrhamnitol.

Still other examples of glycamines (1-amino-1-deoxyketoses and 1-alkylamino-1-deoxyketoses) suitable for this method include those of the formula:

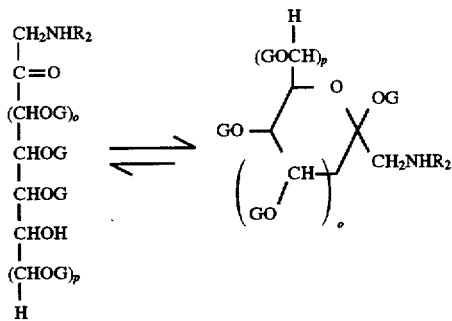

wherein G is hydrogen (H), a $(CH_2CH_2O)_aH$ or $(CH_2CHCH_3O)_bH$ group, a mono-, di-, oligo- or polysaccharide or mixtures thereof: a and b are each from about 0 to about 35 and the sum of a and b are from about 0 to about 35; o is from about 0 to about 2 and p is from about 0 to about 4; and $R^2$ is hydrogen (H), a straight or branched chain saturated or unsaturated hydrocarbon which may be unsubstituted or substituted with a hydroxyl, polyhydroxyl, aromatic, cycloaliphatic or mixed aromatic radical having about 1 to about 31 carbon atoms. These glycamines are described as Amadori rearrangement products and methods for preparing such are disclosed in Methods in Carbohydr. Chem. 2, 99, (1963) to Hodge and Fisher which is incorporated herein by reference. Illustrative of this class include, but are not limited to 1-amino-1-deoxyribulose, 1-amino-1-deoxyxylulose, 1-amino-1-deoxypsicose, 1-amino-1-deoxyfructose(1-amino-1-deoxylevulose), 1-amino-1-deoxyfructose hydrochloride, 1-amino-1-deoxyfructose acetate salt, 1-amino-1-deoxyfructose oxalate salt, 1-amino-1-deoxysorbose, 1-amino-1-deoxytagatose, 1-amino-1-deoxyalloheptulose, 1-amino-1-deoxymannoheptulose, 1-amino-1-deoxysedoheptulose, 1-amino-1-deoxytaloheptulose, 1-amino-1-deoxyglycergalactooctulose, 1-amino-1-deoxyglyceromannooctulose, 1-amino-1-deoxyerythrogalactononulose, galactopyranosyl-β-(1-4)-1-amino-1-deoxyfructose, glucopyranosyl-α-(1-4)-1-amino-1-deoxyfructose, glucopyranosyl-β-(1-4)-glucopyranosyl-β-(1-4)-1-amino-1-deoxyfructose, glucopyranosyl-α-(1-4)-{glucopyranosyl-α-(1-4)}₄-1-amino-1-deoxyfructose, 1-methylamino-1-deoxyfructose hydrochloride, 1-ethylamino-1-deoxyfructose acetate salt, 1-propylamino-1-deoxyfructose oxalate salt, 1-hydroxypropylamino-1-deoxyfructose 1-coconutamino-1-deoxyfructose, 1-tallowamino-1-deoxyfructose, $1-C_1-C_{18}$ alkyloxypropylamino-1-deoxyfructose, $1-C_1-C_{18}$ alkyloxypropylaminopropylamino -1-deoxyfructose, 1-methylamino-1-deoxyfructose, 1-ethylamino-1-deoxyfructose, 1-propylamino-1-deoxyfructose, 1-hexylamino-1-deoxyfructose and 1-octylamino-1-deoxyfructose.

Still other examples of glycamines (6-amino-6-deoxyaldoses, 6-amino-6-deoxyketoses, 6-amino-6-deoxyglycosides, 6-alkylamino-6-deoxyaldoses, 6-alkylamino-6-deoxyketoses, 6-alkylamino-6-deoxyglycosides, etc.) suitable for this method include those of the formula:

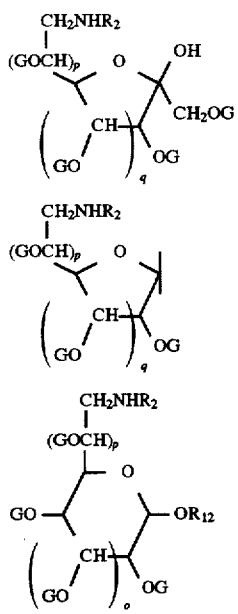

wherein G is hydrogen (H), a $(CH_2CH_2O)_aH$ or $(CH_2CHCH_3O)_b$ group, a mono-, di-, oligo- or polysaccharide or mixtures thereof; $R_2$, is hydrogen (H), or an alkyl, alkenyl or hydroxyalkyl group having about 1 to about 5 carbon atoms; a and b are each from about 0 to about 35 and the sum of a and b are from about 0 to about 35; o is from about 0 to about 2, p is from about 0 to about 4 and q is from about 0 to about 3; and $R_2$ is hydrogen (H), a straight or branched chain saturated or unsaturated hydrocarbon which may be unsubstituted or substituted with a hydroxyl, polyhydroxyl, aromatic, cycloaliphatic or mixed aromatic radical having about 1 to about 31 carbon atoms. Illustrative of this class include, but are not limited to 5-amino-5-deoxyribose, 5-amino-5-deoxyxylose, 6-amino-6-deoxyallose, 6-amino-6-deoxyaltrose, 6-amino-6-deoxyglucose, 6-amino-6-deoxyglucose hydrochloride, 6-amino-6-deoxymethylglucoside, 6-amino-6-deoxyethylglucoside, 6-amino-6-deoxymannose, 6-amino-6-deoxygulose, 6-amino-6-deoxyidose, 6-amino-6-deoxygalactose, 6-amino-6-deoxytalose, 7-amino-7-deoxyglucoheptose, 7-amino-7-deoxyglyceroglucoheptose, 7-amino-7-deoxyglycergalactoheptose, 7-amino-7-deoxyglyceromannoheptose, 6-amino-6-deoxyfructose, 7-amino-7-deoxyalloheptulose, 7-amino-7-deoxymannoheptulose, 7-amino-7-deoxysedoheptulose, 7-amino-7-deoxytaloheptulose, 8-amino-8-deoxyglycerogalactooctulose, 8-amino-8-deoxyglyceromannooctulose, 9-amino-9-deoxyerythrogalactononulose, 9-amino-9-deoxyerythroglucononulose, galactopyranosyl-β-(1-4)-6-amino-6-deoxyglucose, 6-amino-6-deoxygalactose-β-(1-4)-glucopyranose, 6-amino-6-deoxygalactose-β-(1 -4)-6-amino-6-deoxyglucose, glucopyranosyl-α-(1-4)-6-amino-6-deoxyglucose, 6-amino-6-deoxyglucose-α-(1 -4)-glucopyranose, 1-amino-1-deoxy-β-fructofuranosyl-α-glucopyranoside, 6-amino-6-deoxy-β-fructofuranosyl-α-glucopyranoside, β-fructofuranosyl-α-6-amino-6-deoxyglucopyranoside and glucopyranosyl-α-(1-4)-{glucopyranosyl-α-(1-4)}$_5$-6-amino-6-deoxyglucose, 6-methylamino-6-deoxyglucose, 6-ethylamino-6-deoxyglucose, 6-propyl-amino-6-deoxyglucose, 6-butylamino-6-deoxyglucose, 6-coconutamino-6-deoxyglucose, 6-hydroxyethylamino-6-deoxyglucose, 6-methyloxypropylamino-6-deoxyglucose, 6-methylamino-6-deoxymethylglucoside, 6-ethylamino-6-deoxyethylglucoside, 6-propylamino-6-deoxycoconutglucoside, 6-butylamino-6-deoxymethylglucoside, 6-coconutamino-6-deoxyglucoside, 6-hydroxyethylamino-6-deoxypropylglucoside and 6-methyloxypropylamino-6-deoxymethylglucoside.

Yet other examples of glycamines suitable for this method include the Z-amino-Z-deoxyaldoses, Z-alkylamino-Z-deoxyaldoses, Z-amino-Z-deoxyketoses, Z-alkylamino-Z-deoxyketoses, Z-amino-Z-deoxy glycosides and mixtures thereof wherein Z is from about 1 to about 8.

Of the above described glycamines, those of the following formulas are most highly preferred:

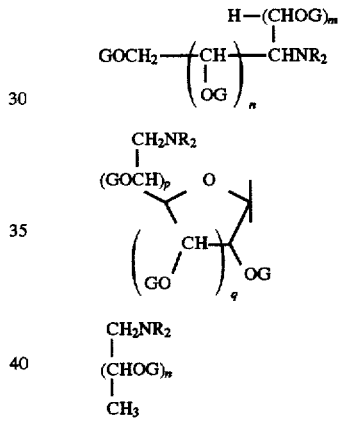

wherein G, $R_2$ n, m, p and q are defined as above.

Many additional examples of glycamines that are useful in the present invention are described in "Carbohydrates" edited by Collins, published by Chapman and Hall Ltd., (1987) and "The Carbohydrates, Chemistry and Biochemistry" edited by Pigman and Horton, 2nd Edition, Volumes IA, IIA IB and IIB, published by Academic Press Inc., (1972); all of which are incorporated herein by reference.

Examples of suitable alkyl lactones that are useful in the present invention include, but are not limited to γ-heptanolactone, γ-octanolactone, δ-octanolactone, γ-nonanolactone, δ-nonanolactone, γ-decanolactone, δ-decanalactone γ-undecanolactone, δ-undecanolactone, ω-undecanolactone(oxacyclododecan-2-one), γ-dodecanolactone, δ-dodecanolactone, δ-tridecanolactone, δ-tetradecanolactone, w-tridecanolactone(oxacyclotridecan-2-one), δ-tetradecanolactone, δ-pentadecanolactone, δ-hexadecanolactone, γ-octadecanolactone and the like.

Example of suitable hydroxy containing fatty acids which can be esterified with lower alcohols ($C_1$–$C_8$ alcohols) useful in the present invention include, but are not limited to glycolic acid, 2-hydroxyisobutyric acid, 2-hydroxy-2-methylbutyric acid, 2-ethyl-2-hydroxybutyric acid, 2-hydroxy-3-methylbutyric acid, 2-hydroxyisocaproic acid, 2-hydroxycaproic acid 10-hydroxydecanoic acid, 12-hydroxydodecanoic acid, 12-hydroxystearic acid, 9,10-dihydroxystearic acid, 9-hydroxystearic acid, 10-hydroxystearic acid, 9,10-dihydroxymyristic acid, 9-hydroxymyristic acid, 10-hydroxymyristic acid, 9,10-dihydroxypalmitic acid, 9-hydroxypalmitic acid, 10-hydroxypalmitic acid and the like.

Still other examples of hydroxy acids that are useful in the present invention include those isolated from natural sources or prepared by the hydrolysis of a α-halo acids, or by acid hydrolysis of cyanohydrins of aldehydes or ketones, or by the hydrolysis of α-nitrato acids with aqueous sulfite solutions. Specific examples of α-hydroxy acids include, but are not limited to glycolic acid (hydroxyacetic acid), DL-lactic acid (2-hydroxypropionic acid), D-lactic acid, L-lactic acid, 2-hydroxybutyric acid, 2-hydroxycaproic acid, 2-hydroxycaprylic acid, 2-hydroxycapric acid, 2-hydroxylauric acid, 2-hydroxymyristic acid, 2-hydroxypalmitic acid, 2-hydroxypalmiticoleic acid, 2-hydroxystearic acid, 2-hydroxyoleic acid, 2-hydroxylinoleic acid, 2-hydroxylinolenic acid, 2-hydroxyricinoleic acid, 2-hydroxygadoleic acid, 2-hydroxyarachidonic acid, 2-hydroxybehenic acid, 2-hydroxycetoleic acid, 2-hydroxyerucic acid and mixtures thereof.

Still other examples of hydroxy acids useful in the present invention include the β-Hydroxy acids (3-hydroxy acids) which are prepared by catalytic reduction of β-keto esters followed by hydrolysis or by the Reformatsky Reaction. Specific examples of β-hydroxy acids include, but are not limited 3-hydroxypropionic acid, 3-hydroxybutyric acid, 3-hydroxycaproic acid, 3-hydroxycaprylic acid, 3-hydroxycapric acid, 3-hydroxylauric acid, 3-hydroxymyristic acid, 3-hydroxypalmitic acid, 3-hydroxypalmitictoleic acid, 3-hydroxystearic acid, 3-hydroxyoleic acid, 3-hydroxylinoleic acid, 3-hydroxylinolenic acid, 3-hydroxyricinoleic acid, 3-hydroxygadoleic acid, 3-hydroxyarachidonic acid, 3-hydroxybehenic acid, 3-hydroxycetoleic acid, 3-hydroxyerucic acid and mixtures thereof.

Still other examples of hydroxy acids useful in the present invention include the γ-hydroxy acid (4-hydroxy acids), δ-hydroxy acids (5-hydroxy acids), aldonic acids, aldoheptonic acids, aldobionic acids, mevalonic acid and their lactones as well as the hydroxydicarboxylic acids such as maleic acid, malic acid, tataric acid, tartronic acid (hydroxypropanedioic acid), phloionic acid (9,10-hydroxyoctadecanedioic acid) and the like.

Still other examples of hydroxy acid useful in the present invention include those obtained by the oxidation of straight chain alkenoic acids. Examples of useful alkenoic acids which may be oxidized to contain one or more hydroxy groups include but are not limited to propenoic (acrylic) acid, trans-2-butenoic acid (crotonic), cis-2-butenoic acid (isocrotonic), 3-butenoic acid (vinylacetic), 2-pentenoic acid (β-ethylacrylic), 3-pentenoic acid (β-pentenoic), 4-pentenoic acid (allylacetic), 2-hexenoic acid (isohydroascorbic), 3-hexenoic acid (hydrosorbic) trans-2-heptenoic acid, 2-octenoic acid, 2-nonenoic acid, trans-4-decenoic acid, cis-4-decenoic acid, 9-decenoic acid (caproleic), 10-undecenoic acid (undecylenic), trans-3-dodecenoic acid (linderic), tridecenoic acid, cis-9-tetradecenoic acid (myristoleic), pentadecenoic acid, cis-9-hexadecenoic acid (cis-9-hexadecenoic), (cis-9-palmitoleic), trans-9-hexadecenoic acid (trans-9-palmitoleic), 9-heptadecenoic acid, cis-6-octadecenoic acid (petroselinic), trans-6-octadecenoic acid (petroselaidic), cis-9-octadecenoic acid (oleic), trans-9-octadecenoic acid (elaidic), cis-11-octadecenoic acid, trans-11-octadecenoic acid, (vaccenic) cis-5-eicosenoic acid, cis-9-eicosenoic acid, (godoleic), cis-11-docosenoic acid (cetoleic), cis-13-docosenoic acid (erucic), trans-13-docosenoic acid (brassidic), cis-15-tetracosenoic acid (selacholeic), cis-17-hexacosenoic acid (ximenic), cis-21-tracontenoic acid (lumequeic), trans-2,6-heptadiennoic acid, linoleic acid, linolenic acid, cis-5,8,11,14,17-eicosapentaenoic acid, cis-4,7,10,13,16,19-docosahexaenoic acid, 2-ethyl-2-hexanoic acid, citronellic acid, undecylinic acid and the like.

Description of the Essential Process Parameters of (I) and (II)

Within the process of the invention (I) and (II), it is desirable to use nearly water-free reaction components, however this is not an essential condition. Also, within the process of the invention, the glycamine can be added progressively to the alkyl lactone or the alkyl lactone can be added progressively to the glycamine, or both reagents can be added at the beginning of the reaction, preferably however, the glycamine is added in full amount to the alkyl lactone. The glycamine can be used in molar excess relative to the alkyl lactone, or the alkyl lactone can be used in molar excess relative to the glycamine, preferably however, as seen in Examples 15 through 17, and 19 through 21, the reagents are used in stoichiometric liquid molar amounts. However, when the molar ratio of glycamine to alkyl lactone is in excess, it may be in slight excess. The molar ratio of glycamine to alkyl lactone may be from about 1.3:1 to about 1.01:1, preferably 1.2:1 to about 1.02:1, more preferably from about 1.1:1 to about 1.03:1, but this is not a necessary condition.

The glycamine is preferably in crystalline to granular form, however solid, flake, paste, gel or liquid forms can be used as well.

The reaction can be performed at above room temperature, however for shorter reaction times elevated temperatures are usually preferred. Favorable reaction temperatures are from about 50° C. to about 200° C., preferably from about 60° C. to about 190° C., most preferably from about 65° C. to about 180° C. The reaction can be carried out under reduced pressure to assist in the removal of solvent or alcohol, however, it is preferably carried out at atmospheric pressure and under an inert gas blanket such as nitrogen, argon or helium, most preferably it is carried out at atmospheric pressure.

A catalyst is generally used to accelerate the rate of the reaction and is generally classified as an organic or inorganic base. Examples of suitable base catalysts useful in the present method include, but are not limited to sodium hydroxide, potassium hydroxide, ammonium hydroxide, calcium hydroxide, magnesium hydroxide, sodium metal, potassium metal, sodium methoxide, potassium methoxide, sodium ethoxide, potassium ethoxide, sodium carbonate, potassium carbonate, ammonium carbonate, magnesium carbonate, calcium carbonate, lithium carbonate, sodium bicarbonate,potassium bicarbonate, ammonium bicarbonate, magnesium bicarbonate, calcium bicarbonate, trisodium phosphate, tripotassium phosphate, tetrasodium pyrophosphate, tetrapotassium pyrophosphate, pentasodium tripolyphosphate, pentapotassium tripolyphosphate, disodium tartrate, dipotassium tartrate, sodium potassium tartrate, trisodium citrate, tripotassium citrate, sodium acetate, potassium acetate, sodium valerate, sodium laurate, potassium laurate, sodium myristate, potassium myristate, sodium stearate, sodium oleate, sodium 12-hydroxy-dodeconate, sodium 2,2-dimethylbutyrate, disodium oxalate, dipotassium soxalate, disodium malonate, dipotassium malonate, disodium succinate, dipotassium succinate, disodium dodecyl succinate,disodium glutarate, dipotassium glutarate, disodium 1,12-dodecanedicarboxylate, trisodium tricarballylate, tripotassium tricarballylate, tetrasodium 1,2, 3,4-butanetetracarboxylate, tetrapotassium 1,2,3,4-butanetetracarboxylate, disodium itaconate, dipotassium itaconate, disodium maleate, dipotassium maleate, disodium fumarate, dipotassium fumarate, disodium malate, disodium agaricate, dipotassium agaricate, sodium ethoxyacetate, sodium glycoxylate, sodium 4-acetylbutyrate, sodium cyclohexylacetate, trisodium 1,3,5-cyclohexanetricarboxylate, sodium basic silicates, potassium basic silicates, sodium basic aluminosilicates, potassium basic aluminosilicates, sodium lactate, potassium lactate, ammonium lactate, sodium glycinate, sodium dimethylglycinate, pentasodium diethylenetriaminepentaacetate (DTPA), tetrasodium ethylenediam inetetraacetate (EDTA), tetrapotassium ethylenediaminetetraacetate, calcium disodium ethylenediaminetetraacetate, triethylamine, tripropylamine, tributylamine, trioctylamine, N,N-dimethyldodecyldfamine, N,N'-diethylethylenediamine, N,N-diethyl-N'-methylethylenediamine, N,N,N',N'-tetramethylenediamine, N,N,N',N'-tetraethylenethylenediamine, N,N,N',N'-tetramethylethylenediamine, N,N,N'N'-tetraethyl-1,2-propanediamine, monethanolamine, diethanolamine, triethanolamine, pyridine, morpholine, picoline, collidine, ethylpiperidine diethylcyclohexylamine and the like. Mixtures of neutralizing agents or base catalysts can be also used as well and may be preferred in certain cases. Preferred base catalysts include sodium hydroxide, sodium methoxide, sodium carbonate, potassium carbonate, sodium bicarbonate, trisodium citrate, sodium laurate, disodium oxalate, triethylamine, tripropylamine, monoethanolamine, diethanolamine and triethanolamine.

The base catalyst can be added at any time during the reaction, however, it is preferably added at the beginning of the reaction and in full amount. The molar ratio of glycamine to base catalyst is from about 500:1 to about 1:1, preferably from about 250:1 to about 5:1, most preferably from about 150:1 to about 10:1.

The substrates are reacted with intensive stirring for several hours, preferably from about 0.5 hour to about 24 hours, more preferably from about 1 hour to about 18 hours, most preferably when the reaction is deemed complete and is verified by an analytical technique such as thin layer chromatography (TLC), infrared spectroscopy (IR), proton nuclear magnet resonance (H1 NMR), carbon 13 nuclear magnet resonance (C13 NMR), direct chemical ionization mass spectrometry (DCI MS), fast atom bombardment mass spectrometry (FAB MS) or high pressure liquid chromatography (HPLC).

In general, water or an organic solvent can be used to perform reactions (I) or (II) of the present invention. The quantity of solvent should be sufficient to dissolve the carbohydrate and the alkyl lactone or alkyl hydroxy ester, but otherwise this is not an essential condition. Typical levels of solvent sued are from about 5% to about 99%, preferably from about 15% to about 80%, most preferably from about 20% to about 60% by weight of the total reaction mixture. Preferably the solvent is removed (after the reaction is complete) by known procedures such as simple distillation, vacuum distillation or rotaevaporation. When water is used, it may be removed by freeze drying, spray drying or vacuum distillation, however, it may be more economical to leave the water in and use it as a diluent making the product a pureable liquid. Typical levels of water used as a reaction solvent or diluent are from about 5% to about 99%, preferably from about 15% to about 75%, most preferably from about 25% to about 60% by weight of the total reaction mixture.

In general, the hydroxy containing alkyl glycamide surfactants of the present invention are usually isolated as solids or semisolids, however, when syrups are obtained, crystallization may be enhanced by the addition of an organic solvent. The resulting product is subsequently filtered, washed with an organic solvent and air or vacuum dried.

Optionally, further purification of solid hydroxy containing alkyl glycamide surfactants can be performed by recrystallization in an organic solvent. The amount of solvent used is sufficient to dissolve the product, preferably with heating. The solution is then slowly cooled until recrystallization is complete,subsequently filtered,washed with an organic solvent and air or vacuum dried.

Typical reaction solvents, crystallization solvents and recrystallization solvents that may be used include, but are not limited to acetic acid, acetone, acetonitrile, butanol, sec-butanol, tert-butanol, butylacetate, butyl chloride, chloroform, cyclohexane, cyclopentane, dimethylformaide (DMF), dimethylacetamide, dimethylsulfoxide (DMSO), 2-ethoxyethanol, ethyl acetate, ethyl ether, ethylene glycol dimethyl ether (glyme), pentane, hexane, heptane, hexadecane, methanol, 2-methoxyethyl acetate, methylethylketone (MEK), methylisoamlylketone, methylisobutylketone, butylmethylketone, diisobutylketone, N-methyl-2-pyrrolidine, petroleum ether, propanol, isopropanol, propylene carbonate, pyridine, tetrachloroethylene, tetrahydrofuran (THF), tetramethylurea, toluene, trichloroethylene, 1,2,2-trichloro-1,2,2-trifluoroethane, 2,2,4-trimethylpentane, xylene, ethanol, pentylacetate, carbon disulfide, 1-chlorobutane , 1,2-dichloroethane, 1,2-dimethoxyethane, glycerol, methylcyclohexane, ethylene glycol, furan, 1,2-dimethoxyethane, propylene glycol, 1-chloro-1,1-difluoroethane, isopropylbenzene (cume), cyclohexanol, cyclohexanone, 4-hydroxy-4-methyl-2-pentanone (diacetone alcohol), diethylene glycol, diisopropyl ether, ethylene glycol monobutyl ether (2-butylethanol), ethylene glycol monomethyl ether (2-methoxyethanol), hexylene glycol, isopentylacetate, isobutylacetate, isopropylacetate, methylacetate, methylethylketone, and the like, however, alcohols are the preferred reaction solvents and acetates or alcohols are the preferred recrystallization solvents. Mixtures of solvents can be used as well and may be preferred in certain cases.

When the reaction is complete, the base catalyst may be optionally neutralized with an organic or inorganic acid. Examples of suitable neutralizing acids include, but are not limited to hydrochloric acid, sulfuric acid, phosphoric acid, boric acid, nitric acid, oxalic acid, malonic acid, glutaric acid, adipic acid, sebacic acid, tricarballylic acid, 1,2,3,4-butanetetracarboxylic acid, itaconic acid, maleic acid, malic acid, fumaric acid, citraconic acid, glutaconic acid, bis (hydroxymethyl)propionic acid, tartaric acid, citric acid, formic acid, lactic acid,acetic acid, benzoic acid, gluconic acid, glucoheptonic acid, lactobionic acid, maltobionic acid, coconut fatty acid, lauric acid, myristic acid, palmitic acid, valeric acid, 2-propylpentanoic acid, succinic acid, dodecenyl succinic acid, arotonic crotonic acid, tiglic acid, glycolic acid, ketomalonic acid, methoxyacetic acid, ethoxyacetic acid, 3-methoxypropionic acid, 6-nitrocaproic acid, levulinic acid, chelidonic acid, cyclobutanecarboxylic acid, 1,1-cyclohexanediacetic acid, glycine, phenylacetic acid, 3-benzoylpropionic acid, S-benzyithioglycolic acid, phenylmalonic acid, 2-hydroxyphenylacetic acid, toluene sulfonic acid, S-sulfobenzoic acid, 5-sulfoisophthalic acid, $C_8$ to $C_{18}$ alkylbenzenesulfonic acid, methanesulfonic acid, ethanesulfonic acid, propanesulfonic acid, $C_8$ to $C_{18}$ alkyl sulfonic acid, 3-hydroxy-1-propane-sulfonic acid, isethionic acid, sulfur trioxide, anionic surfactants in the acid form ion exchange resin and the like. Mixtures of acids can be used as well. Preferred neutralizing acids include hydrochloric acid, sulfuric acid, nitric acid, oxalic acid, citric acid, formic acid, $C_8$ to $C_{18}$ alkyl benzene-sulfonic acid, sulfur trioxide and methanesulfonic acid. The amount of neutralizing acid used will be that which is sufficient to provide a pH in the range of about 4 to about 9, preferably from about 5 to about 8, most preferably about 7. Neutralization may be done in water or in an inert organic solvent or mixtures thereof, at about 0° C. to about 35° C.

Bleaching is sometimes required in either reactions (I) or (II) of the invention, but not always necessary, since compounds of the invention are usually of good color. Bleaching agents or peroxy compounds that may be used to further improve color are hydrogen peroxide, sodium hypochlorite, potassium hypochlorite, calcium hypochlorite, lithium hypochlorite, dibasic magnesium hypochlorite, sodium hypobromite, chlorinated trisodium phosphate, hypochlorous acid, chloride dioxide, sodium percarbonate, potassium percarbonate, sodium perborate monohydrate, sodium perborate tetrahydrate, oxone, t-butyl hydroperoxide, benzoyl peroxide, bis(trimethylsilyl)peroxide, peroxymonosulfate, peroxyformic acid, peroxyacetic acid, peroxytrifluoroacetic acid, peroxybenzoic acid, m-chloroperoxybenzoic acid, peroxyphthalic acid, peroxymaleic acid, peroxypropionic acid, peroxylauric acid and the like. However, hydrogen peroxide and hydrogen peroxide liberating or generating compounds are preferred. Bleaching may be optionally done in water or in an inert organic solvent before or during the reaction or after the reaction is complete, preferably however, bleaching is done after the reaction is complete at about 0° C. to about 50° C. and in water or an organic solvent. Typical levels of bleaching agent are from about 0.01% to about 10%, preferably from about 0.02% to about 7%, even more preferably from about 0.03 to about 5% by weight of the total reaction mixture.

Color improvement may also be carried out in either reactions (I) or (II) of the invention by using reducing agents belonging to two classes.

The first class of agents comprises compounds which include sulfur in the +4 oxidation state and show a negative oxidation relative to hydrogen. Illustrative of this class are salts of sulfite, bisulfite, hydrosulfite (dithionite), metabisulfate (pyrosulfite) and mixtures thereof. Suitable salt counter ions include alkali metal, alkaline earth metal, ammonium, alkyl or hydroxyalkylammonium cations and mixtures thereof. Specific examples include, but are not limited to sodium sulfite, potassium sulfite, calcium sulfite, sodium bisulfite (sodium hydrogen sulfite), potassium bisulfite, sodium hydrosulfite, zinc hydrosulfite, sodium metabisulfite and potassium metabisulfite. Sulfur dioxide, sulfurous acid and sodium sulfoxylate form aldehyde are useful as well.

The second class of reducing agents includes those compounds having hydrogen in the −1 oxidation state and show a negative oxidation potential relative to hydrogen. Illustrative of this class are sodium hydride, potassium hydride, calcium hydride, lithium hydride, magnesium hydride, sodium borohydride, sodium cyano borohydride potassium borohydride, lithium borohydride, magnesium borohydride, alkyl- and alkoxy borohydrides, aluminum hydride, sodium aluminum hydride, potassium aluminum hydride, calcium aluminum hydride, lithium aluminum hydride, alkyl- and alkoxy aluminum hydrides such as sodium dihydro bis(2-methoxyethoxy)aluminate, diboranes and mixtures thereof. Particularly preferred among the foregoing are the bisulfites and borohydrides, most especially preferred are sodium bisulfite and sodium borohydride and mixtures thereof. Reduction may be optionally done in water or in an inert organic solvent before or during the reaction or after the reaction is complete, preferably however, reduction is done without water or an organic solvent and during or after the reaction is complete at about 0° C. to about 200° C. Typical levels of reducing agent are from about 0.01% to about 12%, preferably from about 0.02% to about 9%, even more preferably from about 0.03% to about 7% by weight of the total reaction mixture.

It should be noted that the alkyl lactone reactants can be replaced with lower esters of hydroxy fatty acids. The reaction conditions that were applied to alkyl lactones can be also applied to esters of hydroxy fatty acids.

Home Application and Use

The hydroxy containing alkyl glycamide surfactants useful in a variety of detergent, personal product, cosmetic, oral hygiene, food, pharmacological and industrial compositions which are available in many types and forms. Preferred compositions, however, are detergent compositions.

A classification according to detergent type would consist of heavy-duty detergent powders, heavy duty detergent liquids, light duty liquids (dishwashing liquids), institutional detergents, specialty detergent powders, specialty detergent liquids, laundry aids, pretreatment aids, after treatment aids, presoaking products, hard surface cleaners, carpet cleansers, carwash products and the like.

A classification according to personal product type would consist of hair care products, bath products, cleansing products, skin care products, shaving products and deodorant/antiperspirant products.

Examples of hair care products include, but are not limited to rinses, conditioners, shampoos, conditioning shampoos, antidandruff shampoos, antilice shampoos, coloring shampoos, curl maintenance shampoos, baby shampoos, herbal shampoos, hair loss prevention shampoos, hair growth/promoting/stimulating shampoos, hairwave neutralizing shampoos, hair setting products, hair sprays, hair styling products, permanent wave products, hair straightening/relaxing products, mousses, hair lotions, hair tonics, hair pomade products, brillantines and the like.

Examples of bath products include, but are not limited to bath oils, foam or bubble bathes, therapeutic bathes, after bath products, after bath splash products and the like.

Examples of cleansing products include, but are not limited to shower cleansers, shower gels, body shampoos, hand/body/facial cleansers, abrasive scrub cleansing products, astringent cleansers, makeup cleansers, liquid soaps, toilet soap bars, synthetic detergent bars and the like.

Examples of skin care products include, but are not limited to hand/body/facial lotions, sunscreen products, tanning products, self-tanning products, aftersun products, masking products, lipsticks, lip gloss products, rejuvenating products, antiaging products, antiwrinkle products, anticellulite products, antiacne products and the like.

Examples of shaving products include, but are not limited to shaving creams, aftershave products, preshave products and the like.

Examples of deodorant/antiperspirant products include, but are not limited to deodorant products, antiperspirant products and the like.

A classification according to oral hygiene type would consist of, but is not limited to mouthwashes, pre-brushing dental rinses, post-brushing rinses, dental sprays, dental creams, toothpastes, toothpaste gels, tooth powders, dental cleansers, dental flosses, chewing gums, lozenges and the like.

The hydroxy containing alkyl glycamide surfactants of the present invention are also useful in softening compositions such as liquid fabric softeners, fabric softening rinses, fabric softening sheets, tissue papers, paper towels, facial tissues, sanitary tissues, toilet paper and the like.

A classification according to composition form would consist of aerosols, liquids, gels, creams, lotions, sprays, pastes, roll-on, stick, tablet, powdered and bar form.

Industrial Application and Use

The nonionic sugar based surfactants of the present invention are useful as mild nonionic surfactants that may be used alone or in combination with other surfactants to provide low foam and clarity. More specifically, the nonionic sugar based surfactants of the invention are useful as sole surfactants, cosurfactants, detergents, detergency enhancing agents, low foaming agents, foam modifying agents, wetting agents, solubilizing agents, clarifying agents, lime soap dispersants, antihygroscopic agents, bleach stabilizing agents, flow agents, processing aids, viscosity enhancement agents, softening agents, moisturizers, skin (cell) proliferation agents, enzyme stabilizing agents, and the like. In fact, by simple experimentation, which are well known to those skilled in the art, unique synergies of nonionic sugar based surfactants with essential and optional ingredients can be obtained and determined.

The following Examples further describe and demonstrate the preferred embodiments that are within the scope of the present invention. The Examples are given solely for the purpose of illustration and are not to be construed as being limiting to the present invention since may variations are possible without departing from the spirit and scope of the invention.

EXAMPLES

Analysis of Monosaccharide Hydroxy Containing Alkyl Glycamides by Gas Chromatography Gas chromatography was found to be a convenient method for the examination of monosaccharide hydroxy containing alkyl glycamide compounds. The method of persilylation with hexamethyidisilazane (HMDS) and trimethylchlorosilane (TMCS) in pyridine is the simplest way for producing sufficiently stable and volatile derivatives for analysis. The mixture of both agents are more reactive than either reagent alone, and the by-products combine to form neutral ammonium chloride ($NH_4Cl$) or pyridine hydrochloride($C_5H_5N$-HCl).

The purity of several monosaccharide hydroxy containing alkyl glycamides were determined and found to be 97–99.9%. All products were well separated from starting materials, however glycamides with alkyl chains containing eighteen carbons or more were not volatile enough for analysis.

Approximately 7–10 mg. of a monosaccharide hydroxy containing alkyl glycamide compound was treated with 1 ml of sil-prep reagent (pyridine:HMDS:TMCS=9:3:1) in a 1 dram stoppered vial containing a magnetic stirring bar. The mixture was stirred vigorously at room temperature for about an hour or longer prior to chromatography. The solution became cloudy owing to precipitation of $NH_4Cl$ and $C_5H_5N$·HCl which was filtered through a CAMEO II 25 mm filter. From about 1.0 µl to about 1.1 µl of the resulting mixture was injected into the gas chromatograph.

All gas chromatography was conducted on a Hewlett Packard 5890 Series II Gas Chromatograph. All sample components were detected by a flame ionization detector using a split ratio of 100:1 and separated on a crosslinked 5% phenylmethyl silicone capillary column 25 m×0.32 mm×0.53 µm. The carrier gas was helium at 1 ml/minute and the temperature program was 3 minutes at 140° C. then 30° C./minute to 250° C. for 75 minutes.

Example 1 (Comparative)
Preparation of Dodecyl D-Glucamide

A 500 ml four necked round bottom flask equipped with two addition funnels, thermometer and mechanical stirrer was charged with glucamine (13.9 g, 0.0768 mole) and water (250 ml). The solution was cooled to 10° C. and 10% aqueous sodium hydroxide solution (30.7 g, 0.0768 mole) and lauryl chloride (16.8 g, 0.0768 mole) were simultaneously added over a 1 hour period. During the addition a pH of about 10 was maintained. The solution was stirred for 2 hours at 21° C. and the white product was filtered and washed with cold water (3×100 ml). The product was slurried in cold water (200 ml.) and dried under high vacuum to give 23 g (88% yield), of 99.9% pure dodecyl D-glucamide.

Examples 2–5 (Comparative)

The following compounds were prepared in a similar manner as in Example 1.

| Example | Compound (Comparative) | Yield |
|---|---|---|
| 2 | Tetradecyl D-Glucamide | 86% |
| 3 | Hexadecyl D-Glucamide | 81% |
| 4 | Octadecyl D-Glucamide | 90% |
| 5 | Coconut D-Glucamide | 84% |

Example 6 (Comparative)
Preparation of Dodecyl Methyl D-Glucamide

A 300 ml four necked round bottom flask equipped with two addition tunnels, thermometer and mechanical stirrer was charged with N-methylglucamine (15.0 g, 0.0768 mole) and water (74 g). The solution was cooled to 15° C. 10% Aqueous sodium hydroxide solution (30.7 g, 0.0768 mole) and lauryl chloride (16.8 g, 0.0768 mole) were added simultaneously over a 1 hour period. During the addition a pH of about 10 was maintained. The solution was stirred for 2 hours at 21° C. The sample was dried by freeze drying and enough ethanol was added to dissolve the product. Sodium chloride was removed by vacuum filtration and the product was concentrated on a rotaevaporator. The product was recrystallized in ethanol to give 24 g (83% yield) of 99.9% pure dodecyl methyl D-glucamide.

Example 7 (Comparative)
Preparation of Coconut D-Gluconamide

A 5 liter four necked round bottom flask equipped with a condenser, addition funnel, thermometer and mechanical stirrer was charged with D-glucono-1,5-lactone (480.0 g, 2.69 moles) and methanol (2752 g, for 27% total solids). The suspension was heated to 40°–50° C. for 15 minutes and the heating mantle removed. Cocoamine (538.0 g, 2.69 moles) containing methanol 80 ml) was added dropwise over ½ hour. The reaction mixture was allowed to cool to room temperature (about 21° C.) followed by stirring overnight to allow complete crystallization. The white product was filtered, washed with methanol (3×500 ml) and dried under vacuum at 40°–45° C. giving 947.0 g (93% yield) of coco D-gluconamide with a melting point of 147°–148° C.

Examples 8–14 (Comparative)

The following compounds were prepared in a similar manner as in Example 7.

| Example | Compound (Comparative) | Yield |
|---|---|---|
| 8 | Octyl D-Gluconamide | 90% |
| 9 | Decyl D-Gluconamide | 91% |
| 10 | Dodecyl D-Gluconamide | 96% |
| 11 | Tetradecyl D-Gluconamide | 92% |
| 12 | Hexadecyl D-Gluconamide | 94% |
| 13 | Octadecyl D-Gluconamide | 94% |
| 14 | Dodecyl L-Gluconamide | 95% |

Example 15
Preparation of Dodecyl 5-Hydroxy D-Glucamide in an Organic Solvent A 500 ml round bottom flask equipped with a condenser, thermometer and mechanical stirrer was charged with D-glucamine (10.0 g, 0.055 mole), δ-dodecanolactone (10.45 g, 0.055 mole), methanol (228 g) and sodium methoxide (0.01 g). The mixture was heated to reflux for 48 hours. Methanol was removed via rotaevaporator and mixture was placed under high vacuum to give 24.1 g (98% yield) of crude dodecyl 5-hydroxy D-glucamide.

Example 16
Preparation of Dodecyl 12-Hydroxy Methyl D-Glucamide

A 250 ml round bottom flask equipped with a condenser, thermometer and mechanical stirrer was charged with methyl glucamine, (20.0 g, 0.102 mole), methyl ester of 12-hydroxy dodecanoic acid (23.5 g 0.102 mole) and sodium methoxide (0.05 g). The mixture was heated to 135° C. and a slight vacuum pulled to remove methanol. The reaction mixture was cooled and warm isopropanol (55 g) was added until all had dissolved. The solution was stirred overnight. Solution was filtered, washed with isopropanol and dried under high vacuum to give 29.3 g (73% yield) of 97% pure dodecyl 12-hydroxy methyl D-glucamide.

Example 17
Preparation of Dodecyl 5-Hydroxy D-Glucamide Without an Organic Solvent A 250 ml round bottom flask equipped with a condenser, thermometer and mechanical stirrer was charged with D-glucamine (10.0 g, 0.055 mole), δ-dodecanolactone (10.45 g, 0.055 mole) and sodium methoxide (0.01 g). The mixture was heated to 135° C. for 7 hours and then slurried with isopropanol (200 ml). The solution was cooled to 30° C., filtered and placed under high vacuum to give 15.6 g (75% yield) of 97% pure dodecyl 5-hydroxy D-glucamide.

Example 18
Purification of Dodecyl 5-Hydroxy D-Glucamide From Example 15

A 500 ml round bottom flask equipped with a condenser was charged with dodecyl 5-hydroxy glucamine (15.6 g), methanol (175 ml) and ether (120 ml). The mixture was heated to reflux until all had dissolved. The mixture was cooled slowly to room temperature and stood overnight. The mixture was filtered and washed with methanol ether mixture and dried under high vacuum giving about 10.1 g (65% yield) of 98% pure dodecyl 5-hydroxy D-glucamide.

Example 19
Preparation of Undecyl 4-Hydroxy D-Glucamide

A 250 ml round bottom flask equipped with a condenser, thermometer and mechanical stirrer was charged with D-glucamine (10 g, 0.055 mole) undecanoic-γ-lactone (10.1 g, 0.055 mole) and sodium methoxide (0.01 g). The mixture was heated to 130° C. for 12 hours, cooled to 30° C. and slurried with isopropanol (200 ml). It was then filtered and placed under high vacuum to give (13.3 g, 66% yield) of 95% pure undecyl-4-hydroxy D-glucamide.

Example 20
Preparation of Dodecyl 12-Hydroxy Methyl D-Maltamide

A 250 ml round bottom flask equipped with a condenser, thermometer and mechanical stirrer was charged with methyl maltamine (36.4 g, 0.102 mole), methyl ester of 12-hydroxy dodecanoic acid (23.5 g 0.102 mole) and sodium methoxide (0.05 g). The mixture was heated to 135° C. and a slight vacuum pulled to remove methanol. The reaction mixture was cooled to room temperature and slurried with ether (150 ml). The mixture was then filtered, washed with ether and let air dry to give 43.6 g (77% yield) of dodecyl 12-hydroxy methyl D-maltamide.

Example 21
Preparation of Dodecyl 12-Hydroxy Methyl D-Sorbitanamide

A 250 ml round bottom flask equipped with a condenser, thermometer and mechanical stirrer was charged with methyl sorbitanamide (18.1 g, 0.102 mole), methyl ester of 12-hydroxy dodecanoic acid (23.5 g 0.102 mole) and sodium methoxide (0.05 g). The mixture was heated to 135° C. and a slight vacuum pulled to remove methanol. The reaction mixture was cooled to room temperature and slurried with ether (150 ml). The mixture was then filtered, washed with ether and let air dry to give 33.6 g (87% yield) of dodecyl 12-hydroxy methyl D-sorbitanamide.

Example 22
Krafft Point (Water Solubility Test)

The temperature at and above which surfactants begin to form micelles instead of precipitates is referred to as the Krafft point ($T_k$) and at this temperature the solubility of a surfactant becomes equal to its CMC (numerical value at which micelles are formed).

The appearance and development of micelles are important since detergency (solubilization of soils) by dishwashing liquids, shampoos, detergents, etc., depend on the formation of these aggregates in solution.

The Krafft point was measured by preparing 650 ml of a 0.1% dispersion of surfactant in water by weight. If the surfactant was soluble at room temperature, the solution was slowly cooled to 0° C. If the surfactant did not precipitate out of solution, its Krafft point was considered to be <0° C. (less than zero). If it precipitated out of solution, the temperature at which precipitation occurs was taken as the Krafft point.

If the surfactant was insoluble at room temperature, the dispersion was slowly heated until the solution became homogeneous. It was then slowly cooled until precipitation occurred. The temperature at which the surfactant precipitates out of solution upon cooling was taken as the Krafft point.

The gluconamides which are a similar class of sugar based surfactant were also used for comparative purposes. The structure of several sugar surfactants are as follows:

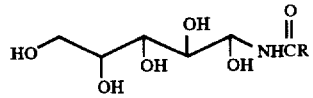

Alkyl Gluconamides (Comparative)

-continued

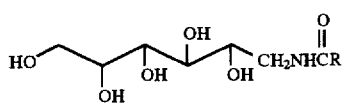

Alkyl Glucamides (Comparative)

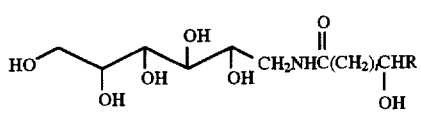

Alkyl Hydroxy Glucamides (The Invention)

wherein R is an alkyl group

Krafft point of Various Sugar Based Surfactants

| Entry | Comparatives | Krafft Point (0.1%) | Micellization and Surface Tension Reduction |
|---|---|---|---|
| A | Octyl D-Gluconamide | 12° C. | Yes |
| B | Decyl D-Gluconamide | 75° C. | Yes |
| C | Dodecyl D-Gluconamide | >100° C. (Insoluble) | No |
| D | Dodecyl L-Gluconamide | >100° C. (Insoluble) | No |
| E | Tetradecyl D-Gluconamide | >100° C. (Insoluble) | No |
| F | Hexadecyl D-Gluconamide | >100° C. (Insoluble) | No |
| G | Coconut D-Gluconamide | >100° C. (Insoluble) | No |
| H | Dodecyl D-Glucamide | >100° C. (Insoluble) | No |
| I | Dodecyl Methyl D-Glucamide | 45° C. | Yes |
| J | Tetradecyl D-Glucamide | >100° C. (Insoluble) | No |
| K | Hexadecyl D-Glucamide | >100° C. (Insoluble) | No |
| L | Octadecyl D-Glucamide | >100° C. (Insoluble) | No |
| M | Coconut D-Glucamide | >100° C. (Insoluble) | No |
| The Invention | | | |
| N | Dodecyl 5-Hydroxy D-Glucamide | 41° C. | Yes |
| O | Undecyl 4-Hydroxy D-Glucamide | 37° C. | Yes |
| P | Dodecyl 12-Hydroxy Methyl D-Maltamide | <21° C. | Yes |

Detailed Discussion of Example 22

From the above table, it can be clearly seen that alkyl aldonamide and alkyl glycamide compounds lacking a hydroxyl group on the hydrocarbon alkyl chain (B—H, J—M) have high Krafft points and are poorly or completely insoluble in water. While not wishing to be bound by theory, it is believed these compounds have an unfavorable heat of hydration, pack closely in the solid state and therefore exhibit high Krafft points and low or no water solubility. However, hydroxy containing alkyl glycamide compounds of the invention which have a hydroxyl group in the hydrocarbon alkyl chains (N—P) have favorably low Krafft points and are highly soluble in water. While not wishing to be bound by theory, it is believed these compounds have a favorable heat of hydration, pack more loosely in the solid state and therefor exhibit favorably low Krafft points and excellent water solubility.

It should be noted that comparative Examples C—H and J—M are insoluble in water and cannot form micelles, nor reduce the surface tension of water whereas, hydroxy containing alkyl glycamide compounds of the invention are highly soluble in water, form micelles and reduce the surface tension of water.

Micellization is the preferred interfacial phenomena, since certain surfactant benefits such as detergency (solubilization of soils), wetting, emulsification etc. depend on the formation of these aggregates in solution. Materials that do not form micelles, as in comparative Examples C—H and J—M, do not provide any detergency, wetting, emulsification benefits.

Thus, the ability of significantly improving the water solubility of an alkyl glycamide while exhibiting micelles for improved surfactant benefits is a significant achievement.

Example 23

Foam Height

Since most of the foaming data on surfactants is typically obtained by the Ross-Miles Foam Height Assay (Ross, J. and Miles, G. D. Am Soc. for Testing material Method D1173-63 Philadelphia, Pa. (1953); Oil & Soap (1958) 62:1260) the foaming ability of these surfactants were acquired using this method.

In the Ross-Miles method, 200 mL of a surfactant solution contained in a pipette of specified dimensions with a 2.9 -mm-i.d. orifice is allowed to fall 90 cm onto 50 mL of the same solution contained in a cylindrical vessel maintained at a given temperature by means of a water jacket. The height of the foam produced in the cylindrical vessel is read immediately after all the solution has run out of the pipette and then again after a given amount of time.

Using this method, the foam production (initial foam height in mm) and foam stability (final foam height after 10 minutes as measured in mm) were measured at 0.1% sugar surfactant concentration, 50° C. and 0 ppm (parts per million) hardness.

Foam Height of Various Sugar Based Surfactants

| Entry | Comparatives | Initial (mm) | Final (mm) (10 min.) | |
|---|---|---|---|---|
| A | Octyl D-Gluconamide | 0 | | 0 |
| B | Decyl D-Gluconamide | 199 | | 6 |
| C | Dodecyl D-Gluconamide | X | Insoluble | X |

-continued

| Entry | Comparatives | Initial (mm) | | Final (mm) (10 min.) |
|---|---|---|---|---|
| D | Dodecyl L-Gluconamide | X | Insoluble | X |
| E | Tetradecyl D-Gluconamide | X | Insoluble | X |
| F | Hexadecyl D-Gluconamide | X | Insoluble | X |
| G | Coconut D-Gluconamide | X | Insoluble | X |
| H | Dodecyl D-Glucamide | X | Insoluble | X |
| I | Dodecyl Methyl D-Glucamide | 173 | | 157 |
| J | Tetradecyl D-Glucamide | X | Insoluble | X |
| K | Hexadecyl D-Glucamide | X | Insoluble | X |
| L | Octadecyl D-Glucamide | X | Insoluble | X |
| M | Coconut D-Glucamide | X | Insoluble | X |
| | The Invention | | | |
| N | Dodecyl 5-Hydroxy D-Glucamide | 67 | | Negligible |
| O | Undecyl 4-Hydroxy D-Glucamide | 60 | | Negligible |
| P | Dodecyl 12-Hydroxy Methyl D-Maltamide | 57 | | Negligible |

X = Compound is insoluble in water, foam height cannot be measured

Detailed Discussion of Example 23

From the above table, it can be clearly seen that alkyl aldonamide and alkyl glycamide compounds lacking a hydroxyl group on the hydrocarbon chain (B—M) exhibit high foam or are insoluble in water. However, hydroxy containing alkyl glycamide compounds of the invention which have a hydroxyl group on the hydrocarbon alkyl chain (N—P) exhibit favorably low foam and are soluble in water.

Thus, the ability of significantly improving water solubility of an alkyl glycamide without exhibiting high foam is a significant achievement. These findings are quite unusual and expected.

Example 24
Foaming of a Prototype Detergent Formulation

A prototype detergent formulation comprising a hydroxy containing alkyl glycamide surfactant was made and tested to an identical formulation containing a non-hydroxy containing alkyl glycamide. The formulation is as follows:

| Ingredients (by weight) | % |
|---|---|
| $C_{10}-C_{14}$ Linear Alkylbenzene Sulfonate | 15 |
| $C_{12}-C_{15}$ Alcohol Ethoxylate Containing 7 Units of EO | 15 |
| Dodecyl 5-Hydroxy D-Glucamide (or Comparative) | 4 |
| Sodium Tripolyphosphate | 30 |
| Sodium Silicate | 10 |
| Sodium Sulfate | 9 |
| Sodium Carbonate | 9 |
| Sodium Carboxymethyl Cellulose | 0.5 |
| Lipase Enzyme | 0.3 |
| Water | Balance |

Using the Ross Miles Foam Height Method, the foam production (initial foam height in mm) and foam stability (foam height after 5 minutes and 10 minutes in mm) were measured at 0.4% formulation concentration, 25° C., 18 FH (2:1 Ca:Mg) hardness.

| Foam Height of Various Formulations | Initial (mm) | 5 min (mm) | 10 min (mm) |
|---|---|---|---|
| Dodecyl Methyl D-Glucamide (Comparative) | 135 | 110 | 100 |
| Dodecyl 5-Hydroxy D-Glucamide | 125 | 94 | 75 |

As can be seen from the above table, formulations containing dodecyl 5-hydroxy D-glucamide are low foaming compared to identical formulations containing dodecyl methyl D-glucamide. This clearly demonstrates the low foaming capacity of hydroxy containing alkyl glycamides of the invention.

Example 25–26 Detergency
Detergency Evaluation of Hydroxy Containing Alkyl Glycamide Compounds It is generally understood that detergency is defined as the cleansing quality or power of a detergent to remove soil and stains. While not wishing to be bound by theory, it is believed that hydroxy containing alkyl glycamide compounds and cosurfactants remove soils together or independently through three different possible modes of action (which is dependent on the type of soil present). The first mode of action involves an effective and efficient lowering of surface tension through micellarization (as in Example 22) which results in a change in the interfacial properties of soil and fabric making the soil more susceptible to removal. The second mode of action is emulsification of greasy dirt or oily soil whereby the greasy dirt or oily soil are broken down into tiny droplets which can be held in suspension (in solution) and rinsed away. The third mode of action is absorption of soil which is an active property of foaming surfactants in which soil particles attach themselves to the surface of bubbles (foam) and are suspended on that surface and off the fabric. A stable persistent foam is required throughout the washing cycle for this mode of action to work effective. While not wishing to be bound to theory, it is believed that hydroxy containing alkyl aldonamide compounds of the invention remove soils by the first mode of action, a lowering of the surface tension of water through micellarization.

A great number of test methods have been developed to determine the performance of detergents and various detergent ingredients. A preferred, well excepted test method involves applying various soils uniformly to a standard cloth under strict specifications yielding an "artificially soiled test cloth", which is then washed under controlled conditions in a Terg-o-tometer (washing machine simulator). The detergency of the surfactant is assessed electronically using a reflectometer (Colorgard 2000). Before washing, the initial reflectance value of the soiled test cloth is measured (front and back) giving a value which is represented as reflectance-soiled ($R_s$). After washing, the final reflectance value of the soiled test cloth is measured (front and back) giving a value which is represented as reflectance-washed ($R_w$). From these values, the differences in reflectance $\Delta R = R_w - R_s$ can be calculated and used as a measure of soil removal. It shall be understood that higher ΔR values suggests better or enhanced detergency.

In general, textiles come in contact with a variety of soils, some of which are complicated mixtures of materials differing in their chemical and physical structure. The selection of a model soil representing a natural "real life" soil is a complicated problem. However, significant progress has been made in the area of fabric washing making artificial soiling more realistic. Since it is not practical to test the surfactant detergency with every possible soil that may be encountered, it must therefore be limited to typical model soils representing the most common natural soils. Artificial soils are usually selected to represent the following four types of common natural soils which includes (1) particulate soils, (2) fatty soils, (3) stains and (4) oily soils.

The detergency evaluation of hydroxy containing alkyl glycamides of the invention were determined on Lever Clay cloth, and WFK 20D cloth. Each of the cloths were soiled with the following materials and used in Examples 25–26.

| Cloth | Soil |
|---|---|
| Lever Clay Cloth | Polyester/cotton cloth (65:35) soiled with an extremely hydrophobic ditallowdiamine cation, kaolinitic clay and quartz (particulate and fatty soil). |

The WFK synthetic pigment consists of:

| | |
|---|---|
| 85.0% | Kaolinite |
| 8.0% | Flame Soot 101 |
| 4.0% | Iron Oxide Black |
| 2.0% | Iron Oxide Yellow |
| 100% | |

The WFK synthetic sebum consists of:

| | |
|---|---|
| 18.0% | Free Fatty Acids |
| 32.8% | Beef Tallow |
| 3.6% | Fatty Acid Triglycerides |
| 18.3% | Lanoline |
| 3.7% | Cholesterol |
| 12.0% | Hydrocarbon Mixture |
| 11.6% | Cutina |
| 100% | |

The following wash conditions were used for Examples 25–26

Wash Conditions for Examples 25–26

| | |
|---|---|
| Apparatus | Terg-o-tometer UR7227 |
| Wash Time | 15 Minutes |
| Agitation | 100 rpm |
| Wash Liquid Level | 1000 ml |
| Surfactant | 0.22 g/l |
| Zeolite 4A | 0.45 g/l |
| Sodium Carbonate | 0.30 g/l |
| pH | 10 |
| Hardness | 120 ppm (2:1 Ca:Mg) |
| Temperature | 50° C. |
| Test Cloth/Pot Ratio | Four 3 × 4 Swatches/Pot |

Unless otherwise indicated, the above detergent conditions were used with varying amounts of surfactant ratio by weight. Each result (ΔR), consists of an average of eight measurements (four swatches; front and back). A "bare" prototype formulation containing the minimum amount of ingredients was used to determine the detergency effects of surfactants on various stains and soils. The prototype formulation is as follows:

Prototype Detergent Formulation used for the Evaluation of Hydroxy Containing Alkyl Glycamides

| Ingredients (by weight) | % |
|---|---|
| Total Surfactant System | 22.68 |
| Zeolite 4A | 46.39 |
| Sodium Carbonate | 30.93 |

The surfactant system was dissolved or slurred in about 15 to 25 ml of water according to the appropriate surfactant ratio and then heated to about 60° C. (if necessary). All surfactant systems were added either as a clear solution or as an opacified mixture.

A fair detergency comparison of glycamides, would be those which contain the same sugar head group and about the same number of carbons in the alkyl chain. The comparison groups for Examples 25–26 are as follows:

Detergency Comparison of Hydroxy Containing Alkyl Glycamides Versus Non-Hydroxy Containing Alkyl Glycamides

| Comparison | Aldonamide | ANC |
|---|---|---|
| 1 | Dodecyl D-Glucamide | 12.0 |
| | Dodecyl 5-Hydroxy D-Glucamides | 12.0 |

ANC = Average Number of Carbons in the Alkyl Chain

The following cosurfactant was used in Examples 25–26:

Cosurfactant Used in the Detergency Evaluation (ΔR) of Hydroxy Containing Alkyl Glycamide Compounds 1) $C_{10}$–$C_{14}$ Alkylbenzene Sulfonate (LAS=Linear Alkylbenzene Sulfonate)
2) $C_{12}$ Alkylbenzene Sulfonate (LAS=Linear Alkylbenzene Sulfonate)

Example 25

Detergency Evaluation (ΔR of Hydroxy Containing Alkyl Glycamides with Linear Alkylbenzene Sulfonate on Lever Clay Cloth

| Lever Clay ΔR | | | | | | | |
|---|---|---|---|---|---|---|---|
| AS/NS (% Ratio by Weight) | T | 100/0 | 95/5 | 90/10 | 75/25 | 50/50 | 25/75 |
| LAS: $C_{12}$ 5-Hydroxyl D-Glucamide | 50 | 10.3 | 11.6 | 11.2 | 10.8 | 10.5 | 10.3 |
| LAS: $C_{12}$ D-Glucamide (Comparative) |  | 10.3 | 10.0 | 9.8 | 10.1 | 10.3 | 10.1 |

AS/NS = Anionic Surfactant/Nonionic Surfactant Ratio
T = Temperature °C.

As can be seen from the above table, dodecyl5-hydroxy glucamide, with the larger ΔR values, generally out performs dodecyl D-glucamide at most surfactant ratios (95/5 to 50/50). Based on the above example, it can be concluded that hydroxy containing alkyl glycamide surfactants effectively remove particulate fatty soil from polyester/cotton cloths, especially in the presence of an anionic surfactant such as LAS.

Example 26

Detergency Evaluation (ΔR) of Hydroxy Containing Alkyl Glycamides with Linear Alkylbenzene Sulfonate on WFK 20D cloth

| WFK 20D ΔR | | | | | | | |
|---|---|---|---|---|---|---|---|
| AS/NS (% Ratio by Weight) | T | 100/0 | 95/5 | 90/10 | 75/25 | 50/50 | 25/75 |
| LAS: $C_{12}$ 5-Hydroxy D-Glucamide | 50 | 16.5 | 17.7 | 17.9 | 16.9 | 17.2 | 16.6 |
| LAS: $C_{12}$ D-Glucamide |  | 16.5 | 16.5 | 16.6 | 16.8 | 16.5 | 16.7 |

AS/NS = Anionic Surfactant/Nonionic Surfactant Ratio
T = Temperature °C.

As can be seen from the above table, dodecyl 5-hydroxy D-glucamide with the larger ΔR values, generally outperforms dodecyl D-glucamide at most surfactant ratios (95/5–50/50). Based on the above example, it can be concluded that hydroxy containing alkyl glycamide surfactants effectively remove particulate fatty oily soil from polyester/cotton cloths, especially in the presence of an anionic surfactant such as LAS.

Example 27

Clarity Enhancement

In order to demonstrate the improved ability of hydroxy containing alkyl glycamide compounds to enhance clarity, several prototype detergent compositions were prepared and their clarity measured at room temperature (~21° C.). The prototype detergent composition is as follows:

Prototype Detergent Compositions Comprising Sodium Lauryl Sulfate and Hydroxy Containing Alkyl Glycamide Compounds

| Ingredients | Wt. | Function |
|---|---|---|
| Sodium Lauryl Sulfate | 15.0% | Cleansing Agent |
| Hydroxy Containing Alkyl Glycamide (or Comparative) | 3.0% | Cleansing Agent |
| Sodium Chloride | 2.0% | Viscosity Cobuilder |
| Distilled Water | 78.0–80.0% |  |
| Total | 100.0% |  |

The above formulations were prepared by admixing the above ingredients in listed order and heating the mixture to about 80° C. with rapid stirring. The mixture was then cooled to about 40° C., placed in a clear jar and stored at room temperature for 6 months. The results are as follows:

The Clarity Enhancement of Prototype Detergent Compositions Comprising Hydroxy Containing Alkyl Glycamide Compounds and Sodium Lauryl Sulfate

| Wt. | Compounds | Appearance (Time) |
|---|---|---|
| 3% | $C_{12}$ D-Glucamide (Comparative) | Precipitate (3 days) |
| 3% | $C_{12}$ 5-Hydroxy D-Glucamide | Clear |

For a clear detergent formulation to be successful it must have good shelf life and should not become turbid or produce sedimentation upon standing. From the above table it can be seen that the detergent compositions comprising glycamide that lack a hydroxyl group on the alkyl chain (dodecyl D-glucamide) do not stay in solution and precipitate out within 3 days whereas, glycamides that contain a hydroxyl group (dodecyl 5-hydroxy glucamide) on the hydrocarbon chain stay in solution and provide clear heavy duty and light duty liquid detergent formulations.

Example 27

Mildness Potential

The zein solubilization assay was developed to determine the biological effects of surfactants on the skin. The protein is normally insoluble in water, but can be brought into solution by interaction with surfactants. The extent of zein dissolved is related to the irritation potential (M. J. Schwinger, Kolloid-Z.Z. Poly., 233, 848, 1969). The greater the zein solubilization, the greater the irritation potential of that surfactant on the skin.

In order to demonstrate the improved ability of hydroxy containing alkyl glycamides to provide mildness benefits to the skin, mixtures of dodecyl 5-hydroxy D-glucamide and sodium lauryl sulfate (SLS) by weight were tested and compared to pure sodium lauryl sulfate. Thus, a 1% solution of surfactant (30 mls) was added to 1.5 g of zein and stirred at room temperature for 1 hours. Residual zein was collected and dried to constant weight. Differences between starting and residual weight were used to calculate % zein solubilized. The results are as follows:

Mildness Potential of Hydroxy Containing Alkyl Glycamide Compounds (Zein Solubilization Assay)

| Active Ratio | % Zein Solubilized |
|---|---|
| 0:100 | 85 |
| 25:75 | 55 |
| 50:50 | 42 |
| 75:25 | 20 |
| 100:0 | 7 |
| No surfactant (Control) | 5 |

As indicated by the above table, the addition of dodecyl 5-Hydroxy D-glucamide to sodium lauryl sulfate results in less zein solubilization. This result suggests that these formulations (25:75 to 100:0) are more mild than sodium lauryl sulfate alone, and so the hydroxy containing alkyl glycamide compounds not only produce low foam and enhance clarity but are also mild to the skin which is especially advantageous in detergent, personal product and oral hygiene compositions.

We claim:

1. A hydroxy-containing alkyl glycamide surfactant having the following formula:

$$\underset{\text{AC(CH}_2)_s\text{(CHOH)}_t R_1}{\overset{O}{\overset{\|}{\phantom{A}}}}$$

wherein A is one of the following structures attached to the carboxyl C=O groups via the nitrogen atom:

$$GOCH_2 - \left( \underset{OG}{\overset{H-(CHOG)_m}{\underset{|}{CH}}} \right)_n - CHNR_2$$

$$\left( \underset{GO}{\overset{CH_2NR_2}{\underset{|}{(GOCH)_p}}} \underset{}{\overset{O}{\underset{CH}{\phantom{X}}}} \right)_q OG$$

G is hydrogen (H), a SO$_3$M, PO$_3$M$_2$, (CH$_2$CH$_2$O)$_a$H or (CH$_2$CHCH$_3$O)$_b$H group, a mono-, di-, oligo- or polysaccharide or mixtures thereof;

M is hydrogen (H), an alkali metal, alkaline earth metal, ammonium, alkyl substituted ammonium or mono-, di-, trialkanolammonium group having about 1 to about 5 carbon atoms;

a=0–35
b=0–35
m=0–8
n=2 to 6
p=0–4
q=0–3
s=1–6
t=1 to 18

R$_1$ is a straight or branched chain alkyl or alkenyl group which may be unsubstituted or substituted with an aromatic, cycloaliphatic or mixed aromatic group having about 1 to about 31 carbon atoms or hydrogen; and R$_2$ is hydrogen (H), a hydroxylalkyl group having about 1 to about 6 carbon atoms, a straight or branched chain, alkyl or alkenyl group which may be unsubstituted or substituted with an aromatic, cycloaliphatic or mixed aromatic aliphatic group having about 1 to about 28 carbon atoms.

2. A hydroxy containing alkyl glycamide according to claim 1 wherein a=0–15
b=0–15
m=0–5
n=2 to 6
p=0–3
q=0–2
s=1–5
t=1 to 15;

R$_1$ is unsubstituted or substituted with a group of 1 to 24 carbons; and

R$_2$ is unsubstituted or substituted with group of 1 to 18 carbons.

3. An alkyl glycamide according to claim 1, which is dodecyl 5-hydroxy D-glucamide having formula:

$$HO\overset{}{\underset{OH}{\phantom{X}}}\overset{OH}{\underset{OH}{\phantom{X}}}\overset{}{\underset{OH}{\phantom{X}}}CH_2NHC(CH_2)_3\overset{O}{\overset{\|}{C}}\underset{OH}{\overset{}{CH(CH_2)_6CH_3}}$$

4. An alkyl glycamide according to claim 1, which is octadecyl-9,10-dihydroxy methyl glucamide having the formula:

$$HO\overset{}{\underset{OH}{\phantom{X}}}\overset{OH}{\underset{OH}{\phantom{X}}}\overset{}{\underset{OH}{\phantom{X}}}CH_2NC(CH_2)_7\overset{O}{\overset{\|}{\phantom{X}}}\underset{CH_3}{\overset{}{CHCH(CH_2)_7CH_3}}\underset{OHOH}{\phantom{X}}$$

5. A cyclic monosaccharide alkyl glycamide according to claim 1 which is undecyl 4-hydroxy D-sorbitan amide having the formula:

$$HO\overset{CH_2NHC(CH_2)_2CH(CH_2)_6CH_3}{\underset{OH}{\phantom{X}}}\overset{O}{\underset{}{\phantom{X}}}\underset{OH}{\phantom{X}}\underset{OH}{\phantom{X}}$$

6. A disaccharide alkyl glycamide according to claim 1 which is octadecyl-9,10-dihydroxy methyl maltamide having the formula:

$$\text{(disaccharide structure)} \quad CH_2NC(CH_2)_7\overset{O}{\overset{\|}{\phantom{X}}}\underset{CH_3}{\overset{}{CHCH(CH_2)_7CH_3}}\underset{OHOH}{\phantom{X}}$$

7. A powdered detergent composition comprising:
(a) 1% to 75% by wt. of a surfactant selected from the group consisting of anionic surfactant, nonionic surfactant, amphoteric surfactant, zwitterionic surfactant, cationic surfactant; and mixtures thereof;
(b) 5% to 80% by wt. builder
(c) 0–30% buffer salt;
(d) 0–30% sulfate;
(e) 0–4% enzyme;
(f) 0.1–50% hydroxy containing alkyl glycamides according to claim 1;
(g) 0–40% bleach system;
(h) water and additional optional ingredients to 100%.

8. A liquid detergent composition comprising
(a) 1% to 75% by wt. of a surfactant selected from the group consisting of anionic surfactant, nonionic surfactant, amphoteric surfactant, zwitterionic surfactant, cationic surfactant; and mixtures thereof;
(b) 5–80% builder;
(c) 0–40% electrolyte;
(d) 0–5% enzyme;
(e) 0–15% enzyme stabilizer;
(f) 0.1–50% hydroxy containing alkyl glycamides according to claim 1;
(g) water and additional optional ingredients to 100%.

9. A process for preparing the alkyl glycamide surfactant of claim 1 comprising reacting an alkyl lactone with glycamine in the presence of a basic catalyst, in the absence or presence of an organic solvent at a temperature of from about 50° C. to 200° C.

* * * * *